US008124587B2

(12) United States Patent
Steinmetzer et al.

(10) Patent No.: US 8,124,587 B2
(45) Date of Patent: Feb. 28, 2012

(54) 2-(AMINOMETHYL)-5-CHLOROBENZYLAMIDE DERIVATIVES AND THEIR USE AS INHIBITORS OF THE CLOTTING FACTOR XA

(75) Inventors: Torsten Steinmetzer, Jena (DE); Daniel Doennecke, Weimar (DE); Andrea Schweinitz, Jena (DE); Anne Stuerzebecher, Weimar (DE); Joerg Stuerzebecher, Erfurt (DE)

(73) Assignee: The Medicines Company (Leipzig) GmbH, Leipzig (DE)

( * ) Notice: Subject to any disclaimer, the term of this patent is extended or adjusted under 35 U.S.C. 154(b) by 453 days.

(21) Appl. No.: 11/991,756

(22) PCT Filed: Sep. 18, 2006

(86) PCT No.: PCT/EP2006/009052
§ 371 (c)(1),
(2), (4) Date: Mar. 10, 2008

(87) PCT Pub. No.: WO2007/031343
PCT Pub. Date: Mar. 22, 2007

(65) Prior Publication Data
US 2009/0117185 A1 May 7, 2009

(30) Foreign Application Priority Data
Sep. 16, 2005 (DE) .......................... 10 2005 044 319

(51) Int. Cl.
*A61K 38/05* (2006.01)
*A61K 38/36* (2006.01)
*A61K 9/28* (2006.01)
*C07D 213/89* (2006.01)
*C12N 9/99* (2006.01)

(52) U.S. Cl. .................. 514/14.4; 514/13.5; 514/21.92; 424/474; 546/337; 435/184

(58) Field of Classification Search .................. None
See application file for complete search history.

(56) References Cited

U.S. PATENT DOCUMENTS

| | | |
|---|---|---|
| 6,515,011 B2 | 2/2003 | Selnick et al. |
| 6,528,503 B2 | 3/2003 | Williams et al. |
| 6,831,196 B2 | 12/2004 | Stürzebecher et al. |
| 6,841,701 B2 | 1/2005 | Stürzebecher et al. |
| 7,038,074 B2 | 5/2006 | Moroder et al. |
| 7,407,982 B2 | 8/2008 | Steinmetzer et al. |
| 2004/0087511 A1 | 5/2004 | Shiraishi et al. |
| 2005/0119190 A1 | 6/2005 | Stürzebecher et al. |
| 2005/0176993 A1 | 8/2005 | Stürzebecher et al. |
| 2006/0148901 A1 | 7/2006 | Stürzebecher et al. |
| 2007/0055065 A1 | 3/2007 | Stürzebecher et al. |
| 2007/0066539 A1 | 3/2007 | Stürzebecher et al. |
| 2010/0022781 A1 | 1/2010 | Steinmetzer et al. |

FOREIGN PATENT DOCUMENTS

| | | |
|---|---|---|
| CA | 2412181 | 12/2002 |
| DE | 42 43 858 | 6/1994 |
| DE | 100 29 014 | 12/2001 |
| DE | 100 29 015 | 12/2001 |
| DE | 102 12 555 | 9/2003 |
| DE | 102 10 590 | 10/2003 |
| DE | 103 01 300 | 7/2004 |
| EP | 0 183 271 | 6/1986 |
| EP | 0 669 317 | 8/1995 |
| EP | 0 672 658 | 9/1995 |
| EP | 1 364 960 | 11/2003 |
| WO | WO 92/08709 | 5/1992 |
| WO | WO 95/29189 | 11/1995 |
| WO | WO 00/64470 | 11/2000 |
| WO | WO 01/96286 | 12/2001 |
| WO | WO 01/96366 | 12/2001 |
| WO | WO 02/06280 | 1/2002 |
| WO | WO 02/06280 A2 | 1/2002 |
| WO | WO 02/14349 | 2/2002 |
| WO | WO 02/50056 A1 | 6/2002 |
| WO | WO 03/076457 A1 | 9/2003 |

OTHER PUBLICATIONS

Definition of Thromboembolism from MedicineNet.com, http://medterms.com/script/main/.art.asp?aticlekey=25032, p. 1. Accessed Jun. 14, 2010.*
Thromboembolism from http://emedicine.medscape.com/article/1267714-overview, pp. 1-4. Accessed Jun. 14, 2010.*
Thromboembolism Treatment from http://emedicine.medscape.com/article/1267714-treatment, pp. 1-6. Accessed Jun. 14, 2010.*
Pulmonary Embolism from Merck manual, pp. 1-17. Accessed Jun. 14, 2010.*
Definition of residue from http://dictionary.reference.com/browse/residue, pp. 1-4. Accesssed Jul. 13, 2009.*
Definition of radical from www.merriam-webster.com/dictionary/free%20radical, pp. 1-2. Accessed Mar. 30, 2009.*
Choi-Sledeski et al., "Discovery of an Orally Efficacious Inhibitor of Coagulation Factor Xa Which Incorporates a Neutral $P_1$ Ligand," *J. Med. Chem.* 46:681-684 (2003).
Fareed et al., "Inhibition of Serine Proteases by Low Molecular Weight Peptides and Their Derivatives", *Ann. N. Y. Acad. Sci.* 370:765-784 (1981).
Gustafsson et al., "Effects of Melagatran, a New Low-Molecular-Weight Thrombin Inhibitor, on Thrombin and Fibrinolytic Enzymes," *Thromb. Haemost.* 79:110-118 (1998).
Gustafsson et al., "Effects of Inogatran, a New Low-Molecular-Weight Thrombin Inhibitor, in Rat Models of Venous and Arterial Thrombosis, Thrombolysis and Bleeding Time," *Blood Coagulation and Fibrinolysis* 7:69-79 (1996).
Gustafsson et al., "The Direct Thrombin Inhibitor Melagatran and Its Oral Prodrug H 376/95: Intestinal Absorption Properties, Biochemical and Pharmacodynamic Effects," *Thromb. Res.* 101:171-181 (2001).

(Continued)

*Primary Examiner* — Julie Ha
(74) *Attorney, Agent, or Firm* — Clark & Elbing LLP

(57) ABSTRACT 2-(Aminomethyl)-5-chlorobenzylamide derivatives and their use as inhibitors of coagulation factor Xa are provided. The compounds are suitable for the treatment and prophylaxis of cardiovascular and thrombotic events.

31 Claims, No Drawings

OTHER PUBLICATIONS

Gustafsson et al., "A New Oral Anticoagulant: The 50-Year Challenge," *Nature Reviews Drug Discovery* 3:649-659 (2004).

Hara et al., "DX-9065a, a New Synthetic, Potent Anticoagulant and Selective Inhibitor for Factor Xa," *Thromb. Haemost.* 71:314-319 (1994).

Herbert et al., "DX 9065A, a Novel, Synthetic, Selective and Orally Active Inhibitor of Factor Xa: In Vitro and In Vivo Studies," *J. Pharmacol. Exp. Ther.* 276:1030-1038 (1996).

Ho et al., "Exploratory Solid-Phase Synthesis of Factor Xa Inhibitors: Discovery and Application of $P_3$-Heterocyclic Amides as Novel Types of Non-Basic Arginine Surrogates," *Bioorg. Med. Chem. Lett.* 9:3459-3464 (1999).

Hooper et al., "Type II Transmembrane Serine Proteases," *J. Biol. Chem.* 276:857-860 (2001).

Kettner et al., "Inactivation of Trypsin-Like Enzymes with Peptides of Arginine Chloromethyl Ketone," *Methods in Enzymology* 80:826-842 (1981).

Kettner et al., "The Selective Inhibition of Thrombin by Peptides of Boroarginine," *J. Biol. Chem.* 265, 18289-18297 (1990).

Kettner et al., "The Selective Affinity Labeling of Factor $X_a$ by Peptides of Arginine Chloromethyl Ketone," *Thromb. Res.* 22:645-652 (1981).

Lee et al., "Noncovalent Tripeptidic Thrombin Inhibitors Incorporating Amidrazone, Amine and Amidine Functions at P1," *Bioorg. Med. Chem. Lett.* 12:1017-1022 (2002).

Maduskuie et al., "Rational Design and Synthesis of Novel, Potent Bis-Phenylamidine Carboxylate Factor Xa Inhibitors," *J. Med. Chem.* 41:53-62 (1998).

Mignatti et al., "Biology and Biochemistry of Proteinases in Tumor Invasion," *Physiological Reviews* 73:161-195 (1993).

Mohan et al., "Solid-Phase Synthesis of N-Substituted Amidinophenoxy Pyridines as Factor Xa Inhibitors," *Bioorg. Med. Chem. Lett.* 8:1877-1882 (1998).

Ohno et al., "FOY: [Ethyl-(6-Guanidinohexanoyloxy) Benzoate] Methanesulfonate as a Serine Proteinase Inhibitor. I. Inhibition of Thrombin and Factor Xa in Vitro," *Thromb. Res.* 19:579-588 (1980).

Ossowski et al., "Antibodies to Plasminogen Activator Inhibit Human Tumor Metastasis," *Cell* 35:611-619 (1983).

Ostrem et al., "Discovery of a Novel, Potent, and Specific Family of Factor Xa Inhibitors via Combinatorial Chemistry," *Biochemistry* 37:1053-1059 (1998).

Phillips et al., "Discovery of N-[2-[5-[Amino(imino)methyl]-2-hydroxyphenoxy]-3,5-difluoro-6-[3-(4,5-dihydro-1-methyl-1H-imidazol-2-yl)phenoxy]pyridin-4-yl]-N-methylglycine (ZK-807834): A Potent, Selective, and Orally Active Inhibitor of the Blood Coagulation Enzyme Factor Xa," *J. Med. Chem.* 41:3557-3562 (1998).

Quan et al., "Bisbenzamidine Isoxazoline Derivatives as Factor Xa Inhibitors," *Bioorg. Med. Chem. Lett.* 7:2813-2818 (1997).

Renatus et al., "Structural and Functional Analyses of Benzamidine-Based Inhibitors in Complex with Trypsin: Implications for the Inhibition of Factor Xa, tPA, and Urokinase." *J. Med. Chem.* 41:5445-5456 (1998).

Reuning et al., "Multifunctional Potential of the Plasminogen Activation System in Tumor Invasion and Metastasis (Review)," *International Journal of Oncology* 13:893-906 (1998).

Robinson et al., "Chapter 9. Anticoagulants: Inhibitors of the Factor VIIa/Tissue Factor Pathway," *Ann. Rep. Med. Chem.* 37:85-94 (2002).

Rubini et al., "Synthesis of Isosteric Methylene-oxy Pseudopeptide Analogues as Novel Amide Bond Surrogate Units." *Tetrahedron* 43(21):6039-6045 (1986).

Sato et al., "Antithrombotic Effects of YM-60828, a Newly Synthesized Factor Xa Inhibitor, in Rat Thrombosis Models and Its Effects on Bleeding Time," *Br. J. Pharmacol.* 123:92-96 (1998).

Sato et al., "YM-60828, a Novel Factor Xa Inhibitor: Separation of Its Antithrombotic Effects From Its Prolongation of Bleeding Time," *Eur. J. Pharmacol.* 339:141-146 (1997).

Satoh et al., "Medicinal Chemical Studies on Synthetic Protease Inhibitors, trans-4-Guanidinomethylcyclohexanecarboxylic Acid Aryl Esters," *Chem. Pharm. Bull.* 33:647-654 (1985).

Schmitt et al., "Clinical Impact of the Plasminogen Activation System in Tumor Invasion and Metastasis: Prognostic Relevance and Target for Therapy," *Thrombosis and Haemostasis* 78:285-296 (1997).

Shi et al., "Identification and Characterization of a Novel Matrix-Degrading Protease from Hormone-Dependent Human Breast Cancer Cells," *Cancer Res.* 53:1409-1415 (1993).

Sperl et al., "Urethanyl-3-Amidinophenylalanine Derivatives as Inhibitors of Factor Xa. X-Ray Crystal Structure of a Trypsin/Inhibitor Complex and Modeling Studies," *Biol. Chem.* 381:321-329 (2000).

Stürzebecher et al., "Synthetic Inhibitors of Bovine Factor Xa and Thrombin Comparison of Their Anticoagulant Efficiency," *Thromb. Res.* 54:245-252 (1989).

Weitz, "New Anticoagulants for Treatment of Venous Thromboembolism," *Circulation*, 110:I-19-I-26 (2004).

Leadley, "Coagulation Factor Xa Inhibition: Biological Background and Rationale," *Curr. Topics in Med. Chem.*, 1: 151-159 (2001).

Maignan & Mikol, "The Use of 3D Structural Data in the Design of Specific Factor Xa Inhibitors," *Curr. Topics in Med. Chem.*, 1: 161-174 (2001).

Morrissette et al., "Low Molecular Weight Thrombin Inhibitors With Excellent Potency, Metabolic Stability, and Oral Bioavailability," *Bioorganic & Med. Chem. Letters*, 14: 4161-4164 (2004).

Nar et al., "Structural Basis for Inhibition Promiscuity of Dual Specific Thrombin and Factor Xa Blood Coagulation Inhibitors," *Structure*, 9: 29-37 (2001).

Nelson et al., "Stereoselective Synthesis of a Potent Thrombin Inhibitor by a Novel P2-P3 Lactone Ring Opening," *J. Org. Chem.*, 69: 3620-3627 (2004).

Pauls et al., "The Design of Competitive, Small-Molecule Inhibitors of Coagulation Factor Xa," *Frontiers in Med. Chem.*, 1: 129-152 (2004).

Perzborn et al., "In Vitro and In Vivo Studies of the Novel Antithrombotic Agent Bay 59-7939—an Oral, direct Factor Xa Inhibitor," *J. Thromb. & Haemost.*, 3: 514-521 (2005).

Quan et al., "Discovery of 1-(3'-Aminobenzisoxazol-5'-yl)-3-trifluormethyl-N-[2-fluoro-4-[(2'- dimethylaminomethyl)imidazol-1-yl]phenyl]-1H-pyrazole-5-carboxamide Hydrochloride (Razaxaban), a Highly Potent, Selective, and Orally Bioavailable Factor Xa Inhibitor," *J. Med. Chem.*, 48: 1729-1744 (2005).

Quan & Smallheer, "The Race to Orally Active Factor Xa Inhibitor: Recent Advances," *Curr. Opin. In Drug Discovery & Development*, 7: 460-469 (2004).

Rittle et al., "Unexpected Enhancement of Thrombin Inhibitor Potency with o-Aminoalkylbenzylamides in the P1 Position," *Bioorganic & Med. Chem. Letters*, 13: 3477-3482 (2003).

Schechter & Berger, "On the Size of the Active Site in Proteases," *Biochem. Biophys. Res. Commun.*, 27: 157-162 (1967).

Stauffer et al., "9-Hydroxyazafluorenes and their Use in Thrombin Inhibitors," *J. Med. Chem.*, 48: 2282-2293 (2005).

Stürzebecher et al., "Synthesis and Structure—Activity Relationships of Potent Thrombin Inhibitors: Piperazides of 3-Amidinophenylalanine," *J. Med. Chem.*, 40: 3091-3099 (1997).

PCT/IB/338; PCT/IB/373; and PCT/ISA/237, Apr. 28, 2008.

* cited by examiner

2-(AMINOMETHYL)-5-CHLOROBENZYLAMIDE DERIVATIVES AND THEIR USE AS INHIBITORS OF THE CLOTTING FACTOR XA

CROSS REFERENCE TO RELATED APPLICATIONS

This application is the U.S. National Stage of International Application No. PCT/EP2006/009052, filed Sep. 18, 2006, which claims benefit of German patent application no. 10 2005 044 319.2, filed Sep. 16, 2005, hereby incorporated by reference.

The invention relates to novel inhibitors of coagulation factor Xa (FXa), their preparation and use for medicaments and for the therapy, prophylaxis and diagnosis of cardiovascular disorders and thromboembolic events.

The heparin-type anticoagulants currently employed clinically, and the vitamin K antagonists do not comply with all the requirements for an "ideal" antithrombotic. For this reason, alternatives are sought in the low molecular weight inhibitors of coagulation enzymes, specifically of thrombin and FXa. A particular advantage of FXa inhibitors compared with thrombin inhibitors might be the smaller tendency to bleeding which has been shown in various animal experiments. Thus, with antithrombotically effective doses there is only a minimal influence on the bleeding time when FXa inhibitors are used (Leadley, R. J. Curr. Topics in Med. Chemistry 1, 151 (2001); and Quan, M. L. & Smallheer, J. M., Curr. Opin. in Drug Discovery & Development 7, 460 (2004)).

Various effective FXa inhibitors have now been developed (Quan, M. L. & Smallheer, J. M., Curr. Opin. in Drug Discovery & Development 7, 460 (2004); Pauls, H. W. et al., Frontiers in Medicinal Chemistry—Online 1, 129 (2004), and Maignan, S. & Mikol, V. Curr. Topics in Med. Chemistry 1, 161 (2001)). The first FXa inhibitors described contained strongly basic groups such as, for example, amidino or guanidino groups in their C-terminal segment.

It has been shown by X-ray structural analyses that these basic groups form a salt bridge with the aspartic acid, which is characteristic of trypsin-like serine proteases, in position 189 of FXa. Owing to these highly charged basic groups, the first-generation FXa inhibitors usually showed only very low bioavailability after oral administration. For this reason, there has been an intensive search in recent years for new FXa inhibitors which no longer have any basic group in their C-terminal segment. A further strategy comprised the development of inhibitors with reduced basicity which are only partly protonated under physiological pH conditions. A third strategy was to develop prodrugs where the basic groups are liberated only after oral intake in the body (Quan, M. L. & Smallheer, J. M., Curr. Opin. in Drug Discovery & Development 7, 460 (2004); Pauls, H. W. et al., Frontiers in Medicinal Chemistry—Online 1, 129 (2004), and Maignan, S. & Mikol, V. Curr. Topics in Med. Chemistry 1, 161 (2001)).

Although the first orally available FXa inhibitors are now undergoing clinical development (Perzborn, E., J. of Thromb. & Haemost. 3, 514 (2005); Quan, M. L., J. Med. Chem. 48, 1729 (2005)), to date no direct FXa inhibitor has received authorization. For this reason there continues to be intensive work on developing novel FXa inhibitors.

The invention is therefore based on the object of indicating an active ingredient suitable for therapeutic uses which inhibits coagulation factor Xa with high activity and specificity and which circulates in the body as long as possible preferably after i.v., s.c. or oral administration. This invention also relates to the provision of a pharmaceutical preparation.

It has become possible in recent years to develop substrate-analogous thrombin inhibitors with a C-terminal 2-(aminomethyl)-5-chlorobenzylamide (Selnick, H. G. et al., WO 02/50056; Rittle, K. E. et al., Bioorg. Med. Chem. Lett. 13, 3477 (2003), Stauffer, K. J. et al., J. Med. Chem. 48, 2282 (2005)). It was possible to observe a significant bioavailability and anti-thrombotic activity for several of the compounds described after oral administration to various experimental animals. It was shown by X-ray structural analysis that the free aminomethyl group of the C-terminal 2-(aminomethyl)-5-chlorobenzylamide residue forms a salt bridge with the glutamic acid residue 192 which is characteristic of thrombin, and thus makes a significant contribution to the inhibitory activity (Rittle, K. E. et al., Bioorg. Med. Chem. Lett. 13, 3477 (2003), Stauffer, K. J. et al., J. Med. Chem. 48, 2282 (2005)).

WO 02/50056 discloses prolinamide derivatives which have a thrombin-inhibiting effect and can be employed for the therapy of embolisms and thromboses. The publication Bioorganic Medical Chemistry Letters (13, 2003, pages 3477-3482, K. E. Rittle et al.) describes benzenesulfonamidopyridinone derivatives which exhibit thrombin-inhibiting properties.

We have surprisingly found that suitably acylated 2-(aminomethyl)-5-chlorobenzylamine of the general formula I

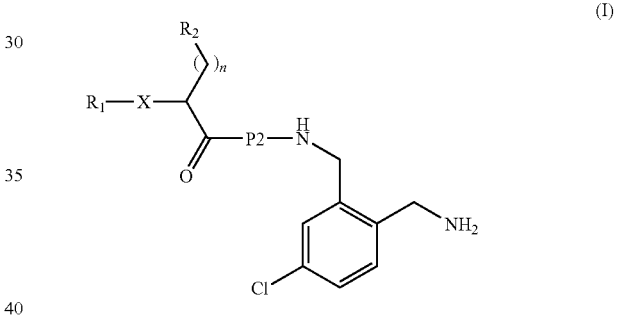

very effectively and selectively inhibits FXa although FXa has, by contrast with thrombin, no glutamic acid in position 192 and therefore the free aminomethyl group of the C-terminal residue cannot form a salt bridge with the 192 residue. Surprisingly, particularly suitable compounds which have a derivative of homophenylalanine in the D configuration as P3 residue, (nomenclature of Schechter and Berger, Biochem. Biophys. Res. Commun. 27, 157 1967)), especially compounds having a P3 residue of the structure II

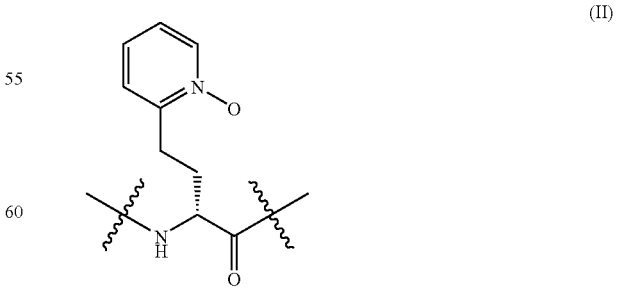

show a distinctly greater inhibitory activity on FXa on comparison of their effect on FXa and thrombin. Further suitable P3 residues proved to be D-homotyrosine or D-homopyridylalanine, where the ring nitrogen can be in the para, meta, or ortho position or be in the form of the N-oxide.

The present invention therefore relates to a compound of the general formula I

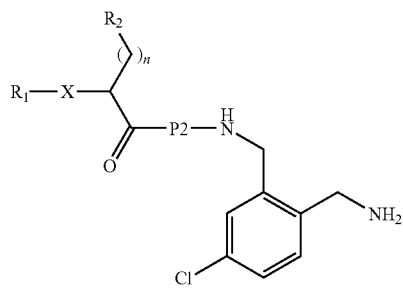

(I)

and pharmaceutically suitable salts of these compounds as inhibitors of coagulation factor Xa, where $X=NR_3$ or O, $R_3$=preferably H, but may also be a branched or unbranched alkyl radical having 1-6 C atoms, in particular alkyl having 1-3 C atoms, especially methyl; with n=0, 1, 2, 3 or 4, preferably with n=1 or 2, in particular n=2;

$R_1$=H, —$CH_2$—$COOR_4$, —$SO_2$—$R_5$, —$COOR_5$ or CO—$R_6$, in particular —$SO_2$—$R_5$;

$R_4$=H or a branched or unbranched alkyl radical having 1-6 C atoms, preferably alkyl having 1 to 3 C atoms, in particular ethyl;

$R_5$=a branched or unbranched alkyl radical having 1-7 C atoms, in particular 1-4 C atoms, which is unsubstituted or substituted by a radical $R_7$, or $R_5$ an aryl or heteroaryl radical which is unsubstituted or substituted by a radical $R_7$, or an aralkyl or heteroaralkyl radical which is unsubstituted or substituted by a radical $R_7$, or a cyclohexylmethyl radical $R_7$=halogen, preferably Cl or F or CN, $NHR_3$, NHCO—$R_3$, —$CH_2$—$NHR_3$, $NO_2$, $OR_3$, $SR_3$, —$COOR_4$ or —$CH_2$—$COOR_4$ and $R_3$ and $R_4$ as defined above $R_6$=a branched or unbranched alkyl radical having 1-8 C atoms, in particular 1-4 C atoms, which is unsubstituted or substituted by a radical $R_7$, or cycloalkyl or a cyclohexylmethyl, but also —$COOR_4$, where $R_4$ is as defined above; and $R_6$ may also be substituted by $R_7$ which is as defined above, and $R_2$=aryl or heteroaryl radical having 5-12 atoms which is unsubstituted or optionally substituted by a radical $R_7$, where the heteroaryl radical may comprise 1-3 heteroatoms such as N, O, or S, and the heteroatom is preferably an N which, if $R_2$ is a pyridyl radical, may also be in the form of pyridine N-oxide, or $R_2$ is a cycloalkyl radical having 5-7 atoms which is unsubstituted or optionally substituted by a radical $R_7$, where one $CH_2$ group of the cycloalkyl radical may be replaced by NH, O or S, and where $R_7$ is defined as described above, P=any natural or unnatural α-amino acid or α-azaamino acid residue of the following structure

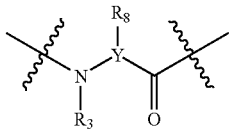

with $R_3$ as defined above, $R_8$=a branched or unbranched alkyl radical having 1-8 C atoms, in particular 1-4 C atoms, which is unsubstituted or substituted by a radical $R_7$, or an aryl or heteroaryl radical which is unsubstituted or substituted by a radical $R_7$, or an aralkyl or heteroaralkyl radical which is unsubstituted or substituted by a radical $R_7$, or a cyclohexylmethyl radical, and where $R_7$ is defined as described above, or Y=CH or N, or P2=any α-imino acid or α-azaimino acid residue of the following structure

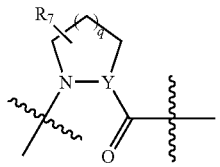

with $R_7$ and Y as defined above and q=0, 1 or 2, and one carbon atom of the ring may be substituted by a radical $R_7$ which is as defined above.

Further particularly suitable compounds are characterized in that $R_1$ is a —$CH_2$—CO—OH, a $CH_2$—CO—$OCH_2CH_3$, or a benzylsulfonyl, a methylsulfonyl, an ethylsulfonyl, an n-propylsulfonyl or an n-butylsulfonyl radical. The benzylsulfonyl group and the groups used in the examples are particularly preferred.

Likewise particularly suitable compounds are characterized in that n is 1 or 2, in particular 2.

The term aryl radical means aromatic radicals familiar to the skilled person such as, for example, phenyl or naphthyl. The term heteroaryl radical means for example 5- or 6-membered heteroaromatic radicals, but also fused heteroaromatic radicals such as quinoline, purine or phenazine. For a more accurate description of heteroaromatic and aromatic systems, reference is made for example to Römpps Chemie-Lexikon, Thieme 1997.

Particularly suitable compounds are characterized in that the amino or the imino acid residue is present with X and $R_2$ in the D configuration.

Likewise particularly suitable compounds are characterized in that P2 is a glycine, a serine, a glutamic acid, an ethyl glutamate, a methyl glutamate or a proline residue.

P2 very particularly preferably means a glycine, serine, glutamic acid, ethyl glutamate or methyl glutamate residue.

In particular, compounds which are eliminated more slowly from the rat circulation are those in which $R_7$ is a —COOH or a —$CH_2$—COOH group, or in which P2 is a glutamic acid residue.

Further examples of preferred compounds or groups of compounds are to be found in the claims.

Pharmaceutically suitable or acceptable salts are particularly suitable for medical applications because of their greater solubility in water compared with the initial or basic compounds. These salts must have a pharmaceutically acceptable anion or cation. Suitable pharmaceutically acceptable acid addition salts of the compounds of the invention are for examples salts of inorganic acids such as hydrochloric acid, hydrobromic, phosphoric, methaphosphoric, nitric, sulfonic and sulfuric acid or organic acids such as, for example, acetic acid, benzenefulfonic, benzoic, citric, ethanesulfonic, fumaric, gluconic, glycolic, isethionic, lactic, lactobionic, maleic, methane-sulfonic, succinic, p-tuluonsulfonic, tartaric and trifluoroacetic acids. It is particularly preferred to use the chlorine salt for medical purposes. Examples of suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise belong within the context of the invention as useful intermediates for preparing or purifying pharmaceutically acceptable salts and/or for use in non-therapeutic, for example in vitro, applications.

The term "physiologically functional derivative" used hereinafter refers to any physiologically tolerated derivative of a compound of the invention of the formula I, e.g. an ester which is able under administration to a mammal such as, for example, a human to form (directly or indirectly) a compound of the formula I or an active metabolite thereof. Physiologically functional derivatives also include prodrugs of the compound of the invention. Such prodrugs can be metabolized in vivo to a compound of the invention. These prodrugs may themselves be active or not.

The compounds of the invention can also exist in various stereoisomeric forms but also in polymorphous forms, e.g. as amorphous and crystalline polymorphous forms. All polymorphous forms of the compounds of the invention, and the stereoisomers, belong in the context of the invention and are a further aspect of the invention.

All references to compounds of formula (I) hereinafter refer to compounds) of the formula (I) as described above, and salts, solvates and physiologically functional derivatives as described herein.

Methods for Analyzing the Compounds

Analytical HPLC

Used for the analytical reversed-phase HPLC was a Shimadzu LC-10A HPLC system consisting of the subsystems CTO-10AS column oven, LC-10AD pumps (2), DGU-14A degasser, SIL-10AD autoinjector, SCL-10A system controller, SPD-10A UV-Vis detector and a Luna 5 μm C18(2) 100 Å, 250 4.6 mm, column from Phenomenex, using the relevant software Shimadzu CLASS-VP, version 5.3. Detection took place at 220 nm. The eluent used was water with 0.1% TFA (A) and acetonitrile with 0.1% TFA (B) at a flow rate of 1 ml/min and a linear gradient (1% B/min).

Preparative HPLC

Used for the preparative RP-HPLC was a Shimadzu HPLC system consisting of the subsystems LC-8A preparative pumps (2), DGU-14A degasser, FRC-10A fraction collector, SCL-10A system controller, SPD-10A UV-Vis detector and a Luna 5 μm C8(2) 100 Å, 250 30.0 mm, column from Phenomenex, using the relevant software Shimadzu CLASS-VP, version 5.3. Detection took place at 220 nm. The eluent used was likewise water with 0.1% TFA (A) and acetonitrile with 0.1% TFA (B) at a flow rate of 10 or 20 ml/min and a suitable gradient.

Mass Spectroscopy

The mass spectra were recorded in an ESI-MS LCQ from Finnigan (Bremen, Germany).

Thin-Layer Chromatography

Adamant $UV_{254}$ precoated silica gel plates from Macherey-Nagel were used for the thin-layer chromatography. The mobile phase was a mixture of n-butanol, glacial acetic acid and water (4:1:1). The compounds were detected by UV absorption at 254 nm and, in addition, a ninhydrin solution (300 mg of ninhydrin dissolved in 100 ml of n-butanol and 3 ml of glacial acetic acid) and, after incubating the TLC plate in a chlorine atmosphere, an o-tolidine solution (150 mg of o-tolidine and 2.1 g of KI dissolved in 2 ml of glacial acetic acid and 148 ml of water) were used as spray reagents.

NMR Spectrometry

The NMR spectra were recorded using a Bruker Avance DPX 300 spectrometer. For this purpose, the samples were dissolved where possible in $D_2O$, otherwise in chloroform-d ($CDCl_3$). The chemical shifts have been indicated in ppm and refer to the solvent signals.

The present invention thus also relates to the use of the compounds of the formula (I) as inhibitors of factor Xa.

The invention also relates to a pharmaceutical composition comprising a compound of the formula (I). The amount of the compound of the formula (I) which is necessary in order to achieve the desired biological effect depends on a number of factors, e.g. the specific compound chosen, the intended use, the mode of administration and the clinical condition of the patient.

The daily dose is generally in the range from 0.03 mg to 100 mg (typically from 3 mg to 50 mg) per day per kilogram of body weight, e.g. 3-10 mg/kg/day. An intravenous dose may be for example in the range from 0.03 mg to 1.0 mg/kg, which can suitably be administered as infusion of from 10 ng to 100 ng per kilogram per minute. Suitable infusion solutions for these purposes may comprise for example from 0.1 ng to 10 mg, typically from 1 ng to 10 mg, per milliliter. Single doses may comprise for example from 1 mg to 10 g of the active ingredient. Thus, ampoules for injections may comprise for example from 1 mg to 100 mg, and single-dose formulations which can be administered orally, such as, for example, tablets or capsules, may comprise for example from 1.0 to 1000 mg, typically from 10 to 600 mg. In the case of pharmaceutically acceptable salts, the aforementioned weight data refer to the weight of the free compound from which the salt is derived. For the prophylaxis or therapy of the abovementioned conditions it is possible for the compounds of the formula (I) to be used themselves as compound, but they are preferably present together with an acceptable carrier or excipient in the form of a pharmaceutical composition. The carrier or excipient must, of course, be acceptable in the sense that it is compatible with the other ingredients of the composition and is not harmful for the patient's health.

The carrier may be a solid or a liquid or both and is preferably formulated with the compound as single dose, for example as tablet which may comprise from 0.05% to 95% by weight of the active ingredient. Further pharmaceutically active substances may likewise be present, including further compounds of the formula (I). The pharmaceutical compositions of the invention can be produced by one of the known pharmaceutical methods, which essentially consist of mixing the ingredients with pharmacologically acceptable carriers and/or excipients.

Pharmaceutical compositions of the invention are in particular those suitable for oral, rectal, topical, peroral (for example sublingual) and parenteral (e.g. subcutaneous, intramuscular, intradermal or intravenous) administration, although the most suitable mode of administration depends in each individual case on the nature and severity of the condition to be treated and on the nature of the compound of formula (I) used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); in the form of powders or granules; as solution or suspension in an aqueous or nonaqueous liquid; or in the form of an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary.

Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, lubricant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain a compound of formula (I) with a flavoring, normally sucrose or gum arabic or tragacanth, and pastilles which comprise the administration of an inert base such as gelatin and glycerol or sucrose and gum arabic.

Pharmaceutical compositions suitable for parenteral administration comprise preferably sterile aqueous preparations of a compound of formula (I), which are preferably isotonic with the blood of the intended recipient. These preparations are preferably administered intravenously, although administration can also take place by subcutaneous, intramuscular or intradermal injection. These preparations can preferably be produced by mixing the compound with water, and making the resulting solution sterile and isotonic with blood. Injectable compositions of the invention generally comprise from 0.1 to 5% by weight of the active compound.

Concerning further formulation, reference is made to customary handbooks.

The invention also relates to processes for producing pharmaceutical compositions in which one or more compounds of the general formula (I) are mixed with suitable carriers and excipients (see above).

Abbreviations Used

| Ac | acetyl |
| Amb | amidobenzyl |
| Ame | aminomethyl |
| aPTT | activated partial thromboplastin time |
| Boc | tert-butyloxycarbonyl |
| Bz | benzoyl |
| Bzl | benzyl |
| Bzls | benzylsulfonyl |
| DIEA | diisopropylethylamine |
| DCM | dichloromethane |
| DMF | N,N-dimethylformamide |
| HPLC | high performance liquid chromatography |
| iPr | iso-propyl |
| i.V. | in vacuo |
| mCPBA | 3-chloroperbenzoic acid |
| MS | mass spectroscopy |
| NMM | N-methylmorpholine |
| NMR | nuclear magnetic resonance spectroscopy |
| PyBOP | benzotriazol-1-yl-N-oxy-tris(pyrrolidino)-phosphonium hexafluorophosphate |
| PT | prothrombin time |
| RT | room temperature |
| tBu | tert-butyl |
| TEA | triethylamine |
| Tfa | trifluoroacetyl |
| TFA | trifluoroacetic acid |
| THF | tetrahydrofuran |
| TMS-Cl | trimethylsilyl chloride |
| TT | thrombin time |

The invention is explained in more detail by the following examples.

EXAMPLE 1

Synthesis of the Inhibitors

Inhibitor 1

Bzls-d-hAla(2-Pyr-NO)-Gly (2-aminomethyl-5-chloro)-benzylamide TFA

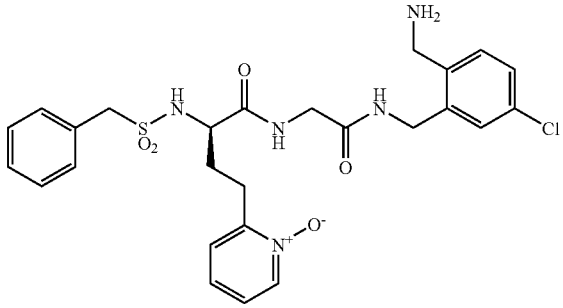

1a) 3-(2-Pyridyl)propanal 35 ml (0.41 mol) of oxalyl chloride were dissolved in 700 ml of dry DCM and cooled to −70° C. A mixture of 62 ml (0.87 mol) of DMSO and 40 ml of dry DCM was added dropwise to this solution over a period of 25 min. During this, the temperature was kept strictly below −65° C. (exothermic reaction). After stirring at −70° C. for 15 min, 50 g (0.36 mol) of freshly distilled 3-(2-pyridyl)propanol dissolved in 150 ml of dry DCM were added dropwise at below −65° C. over a period not exceeding 15 min. 218 ml (0.37 mol) of TEA were added in 40 min, and then the mixture was slowly warmed to RT. 190 ml of water were added to dissolve the salts which had formed. The phases were separated, the DCM phase was concentrated in vacuo, and the product was then purified by distillation (2 mbar, 59-70° C.).

Yield: 33.6 g (0.25 mol, 61%) of colorless oil,

TLC: $R_f$ 0.20.

1b) H-d,l-hAla(2-Pyr)-OH 67 g (0.5 mol) of 1a were mixed with 18 ml of diethyl ether and cooled to 0° C. 88.4 g (1.65 mol) of ammonium chloride were dissolved in 300 ml of water and slowly added to the 2-pyridyl-3-propanal solution. 74.3 g (1.4 mol) of sodium cyanide, dissolved in 200 ml of water, were added to the mixture. The mixture was stirred at 0° C. for 4 h, then heated at 50° C. for 4 h and cooled to RT again. The mixture was extracted 4 with 800 ml of chloroform, and the combined chloroform phases were concentrated in vacuo. The residue was taken up in 1 l of concentrated HCl and stirred at RT for 42 h and then boiled under reflux for 35 h. The solvent was removed in vacuo, the residue was mixed with water and the mixture was concentrated again in vacuo several times. The remaining residue was dissolved in 1.5 l of ethanol and cooled to 4° C. The precipitated salts were removed. The mother liquor was concentrated and purified in 2 portions on an acidic ion exchanger (Dowex® 50WX8-200, ammonium form, 10 cm 15 cm). The product was eluted with 0.2N ammonia solution. The resulting fractions were concentrated in vacuo, and the product was precipitated by adding acetone and was filtered off with suction on a frit and dried in vacuo.

Yield: 42 g (0.233 mol, 47%) of pale brown solid,
HPLC: 4.9% B,
DC: $R_f$ 0.04.
$^1$H NMR, 500.13 MHz, $D_2O$, σ ppm: 8.34 d, broad, $^3J\{HH\}$=5 Hz, 1H, 7.72 ddd $^3J\{HH\}$=7.8 Hz, $^3J\{HH\}$=7.3 Hz, $^4J\{HH\}$=1.5 Hz, 1H, 7.27 d $^3J\{HH\}$=7.8 Hz, 1H, 7.23 dd $^3J\{HH\}$=5 Hz, $^3J\{HH\}$=7.3 Hz, 1H, 3.78 t $^3J\{HH\}$=6.3 Hz, 1H, 2.84 m 2H, 2.18 m 2H. $^{13}$C NMR, 125.75 MHz, $D_2O$, σ ppm: 174.00; 158.80; 147.84; 138.08; 123.52; 121.99; 54.16; 32.38; 30.23.

1c) Bz-d,l-hAla(2-Pyr)-OH 17.7 g (98.22 mmol) of H-d,l-hAla(2-Pyr)-OH were dissolved in 60 ml of dioxane and 60 ml of water and, at 0° C. 17.95 ml (103.14 mmol) of DIEA were added. 11.97 ml (103.14 mmol) of benzoyl chloride were dissolved in 20 ml of dioxane and slowly added dropwise, likewise at 0° C. The mixture was stirred at RT overnight and then the solvent was removed in vacuo. The residue was partly dissolved in a little glacial acetic acid, and ethyl acetate was added. The product crystallized at 4° C.

Yield: 23.3 g (81.9 mmol, 83%) of white crystalline solid
HPLC: 20.5% B.

1d) Bz-d,l-hAla(2-Pyr)-OMe 23.3 g (81.9 mmol) of Bz-d,l-hAla(2-Pyr)-OH were suspended in 35 ml of dry methanol and cooled to −10° C. 8.9 ml (122.85 mmol) of thionyl chloride were added in portions, and the mixture was stirred at −10° C. for 30 min. Then a further 3 ml (40.95 mmol) of thionyl chloride were added. The mixture was warmed to RT and stirred overnight, and the solvent was removed in vacuo. The residue was dissolved with 800 ml of ethyl acetate, washed 2 with 200 ml of saturated $NaHCO_3$ solution and dried with $Na_2SO_4$. The solvent was removed in vacuo, and the residue was dried.

Yield: 18.3 g (61.3 mmol, 75%) of amorphous solid
HPLC: 23.7% B.

1e) Bz-d-hAla(2-Pyr)-OMe 6.3 g (21.1 mmol) of Bz-d,l-hAla(2-Pyr)-OMe were dissolved in 200 ml of methanol, and 750 ml of 0.2N ammonium acetate solution (pH 7.8) were added. The pH was adjusted to 7.5-8 with dilute ammonia solution. 25 mg of α-chymotrypsin (from bovine pancreas, Merck, 350 U/mg), dissolved in 1 ml of water, were added to the mixture. The mixture was incubated at 37° C. for 3 days. During this, the pH was checked regularly and kept constant at pH 7.5-8 by adding dilute ammonia solution. The mixture was then adjusted to pH 4 with acetic acid, the solvent was concentrated in vacuo, and the residue was dissolved in 2M acetic acid. The product was precipitated by adding concentrated ammonia solution at pH 8-9 and was filtered off with suction on a frit, washed with small amounts of aqueous ammonia, pH 8.5, and dried in vacuo. In addition, the basic aqueous phase was extracted 3 with ethyl acetate in order to isolate product still present in the aqueous phase. The ethyl acetate phase was dried with $Na_2SO_4$, and the solvent was removed in vacuo.

Yield: 2.65 g (8.9 mmol, 42%) of pale solid
HPLC: 23.7% B

1f) H-d-hAla(2-Pyr)-OH 6 g (2.0 mmol) of Bz-d-hAla(2-Pyr)-OMe were dissolved in 100 ml of 6N HCl and heated under reflux (oil bath 145° C.) for 20 h. After cooling to RT, the precipitated benzoic acid was filtered off, the solvent was removed in vacuo, the residue was dissolved in water and the mixture was concentrated in vacuo 2. The residue was purified on an acidic ion exchanger (Dowex® 50WX8-200, ammonium form, 10 cm 15 cm). The product was eluted with 0.2N ammonia solution. The resulting fractions were concentrated in vacuo, and the product was precipitated by adding acetone, and was filtered off with suction on a frit and dried in vacuo.

Yield: 1.93 g (1.1 mmol) of white solid (97% isomerically pure, check with Marfey's reagent)
HPLC: 4.9% B
TLC: $R_f$ 0.04.

1 g) Bzls-d-hAla(2-Pyr)-OH TFA 1.97 g (10.9 mmol) of H-d-hAla(2-Pyr)-OH were introduced into 50 ml of DCM and, after addition of 3.04 ml (24.05 mmol) of TMS-Cl (Merck) and 4.12 ml (24.05 mmol) of DIEA (Fluka), heated under reflux for one hour. The now completely clear mixture was then cooled to room temperature, and 2.18 g (11.5 mmol) of benzylsulfonyl chloride (Acros) and 1.96 ml (11.45 mmol) of DIEA were added. Finally, the pH was adjusted to 7.5 with additional DIEA and stirred at room temperature for three hours. The solvent was removed in vacuo and, without further prepurification, the mixture was purified by preparative reversed phase HPLC and lyophilized.

Yield: 1.74 g (3.88 mmol) of white solid
HPLC: 24.9% B.
$^1$H NMR, 300.13 MHz, $D_2O$, σ ppm: 8.62 d, broad, $^3J\{HH\}$=6.0 Hz, 1H, 8.49, dd $^3J\{HH\}$=7.9 Hz, $^3J\{HH\}$=7.4 Hz, 1H, 7.90 dd $^3J\{HH\}$=7.4 Hz, $^3J\{HH\}$=6.0 Hz, 1H, 7.87 d $^3J\{HH\}$=6.0 Hz, 1H, 7.42 m 5H, 4.49 s 2H, 3.84 dd $^3J\{HH\}$=8.2 Hz, $^3J\{HH\}$=5.2 Hz, 1H, 3.13 t $^3J\{HH\}$=7.6 Hz, 2H, 2.21 m 2H. $^{13}$C NMR, 75.48 MHz, $D_2O$, σ ppm: 174.53; 163.08 q $^2J\{CF\}$=35.7 Hz; 155.55; 147.42; 141.19; 131.26; 129.45; 129.33; 128.87; 127.68; 125.55; 116.72 q $^1J\{CF\}$=292.0 Hz; 59.65; 55.83; 31.56; 29.53.

1h) Bzls-d-hAla(2-Pyr)-Gly-OtBu 1.705 g (3.80 mmol) of Bzls-d,l-hAla(2-Pyr)-OH TFA and 0.637 g (3.80 mmol) of H-Gly-OtBu HCl were dissolved in 50 ml of DMF and cooled to 0° C., and 1.979 g (3.80 mmol) of PyBOP and, in portions, 1.95 ml (11.4 mmol) of DIEA were added. The mixture was stirred at 0° C. for 1 h and at room temperature for a further 3 h. The solvent was then removed in vacuo, and the mixture was taken up in a minimal amount of 2M acetic acid, brought to pH 8.5 with concentrated aqueous ammonia solution and extracted three times with ethyl acetate. The combined organic phases were dried over $Na_2SO_4$, filtered and concentrated in vacuo.

Yield: 3.01 g (crude product, oil)

HPLC: 36.9% B.

1i) Bzls-d-hAla(2-Pyr-NO)-Gly-OtBu 3.01 g (crude product) of 1 h were dissolved in 50 ml of DCM and oxidized with 0.933 g (3.80 mmol) of m-CPBA (Fluka, 70%). A further 1.51 g (6.12 mmol) of m-CPBA were introduced in portions over a period of 8 h. The solvent was then removed in vacuo, and the residue was dissolved in a minimum amount of 2M acetic acid, brought to pH 8.5 with concentrated aqueous ammonia solution and extracted 3 with ethyl acetate. The combined organic phases were dried over $Na_2SO_4$, filtered and concentrated in vacuo.

Yield: 2.8 g of oil (crude product)

HPLC: 42.8% B

1j) Bzls-d-hAla(2-Pyr-NO)-Gly-OH 2.8 g of 1i were dissolved in 10 ml of 90% TFA and shaken for 45 minutes. The solvent was then concentrated in vacuo, and the mixture was lyophilized from water.

Yield: 1.35 g (3.3 mmol) of amorphous solid

HPLC: 26.8% B

1) Bzls-d-hAla(2-Pyr-NO)-Gly (2-aminomethyl-5-chloro)-benzylamide TFA 52 mg (0.127 mmol) of Bzls-d-hAla(2-Pyr-NO)-Gly-OH and 35 mg (0.127 mmol) of H-Amb(2-Boc-amidomethyl, 5-Cl) (Nelson, T. D. et al., J. Org. Chem. 69 3620 (2004)) were dissolved in 2 ml of DMF and, at 0° C., 66 mg (0.127 mmol) of PyBOP and 42 µl (0.254 mmol) of DIEA were added. The mixture was stirred at 0° C. for 20 minutes and at room temperature for a further 60 minutes. The solvent was then removed in vacuo, and the remaining residue was dissolved in 1 ml of 90% TFA. The mixture was left for 45 minutes, with occasionally shaken, then concentrated to dryness in vacuo and, without further prepurification, purified by preparative reversed phase HPLC and lyophilized.

Yield: 49 mg (0.072 mmol) of lyophilized powder

HPLC: 31.3% B

MS: calc.: 559.17. found: 560.2 $(M+H)^+$

Inhibitor 2

Bzls-d-hAla(2-Pyr-NO)-Ser (2-aminomethyl-5-chloro)-benzylamide TFA

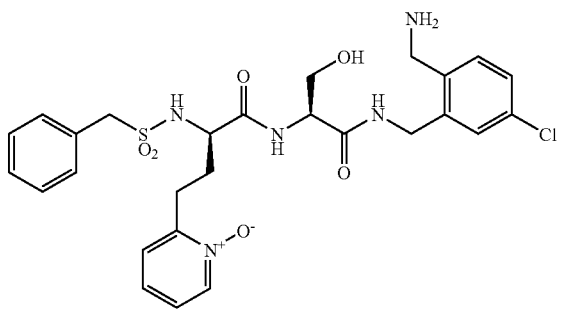

2a) Bzls-d,l-hAla(2-Pyr)-Ser(tBu)-OtBu 80.6 mg (0.180 mmol) of Bzls-d,l-hAla(2-Pyr)-OH TFA and 45.6 mg (0.180 mol) of H-Ser(tBu)-OtBu HCl were dissolved in 4 ml of DMF and, at 0° C., 93.5 mg (0.180 mmol) of PyBop and 123 µl (0.719 mmol) of DIEA were added. The mixture was stirred at 0° C. for 20 min and at room temperature for a further 40 min. The solvent was then removed in vacuo, and the residue was taken up in ethyl acetate, washed 2 with saturated $NaHCO_3$ solution and dried over $Na_2SO_4$. The solvent was removed in vacuo.

Yield: 148 mg of pale yellow oil (crude product)

HPLC: 49.47% B and 49.81% B (diastereomers)

2b) Bzls-d,l-hAla(2-Pyr-NO)-Ser(tBu)-OtBu 148 mg of Bzls-d,l-hAla(2-Pyr)-Ser(tBu)-OtBu (crude product) were dissolved in 40 ml of DCM dried over molecular sieve A4 and, after addition of 40.3 mg (0.180 mmol) of mCPBA (70%), stirred at room temperature for one hour. A further 40.3 mg (0.180 mmol) of mCPBA were added in portions over the course of a further hour. The solvent was removed in vacuo, and the residue was taken up in ethyl acetate, washed 2 with saturated $NaHCO_3$ solution and 1 with saturated NaCl solution and dried over $Na_2SO_4$. The solvent was removed in vacuo.

Yield: 142 mg of pale yellow oil (crude product).

HPLC: 55.39% B and 55.87% B (diastereomers)

2c) Bzls-d,l-hAla(2-Pyr-NO)-Ser-OH 142 mg of Bzls-d,l-hAla(2-Pyr)-Ser(tBu)-OtBu (crude product) were dissolved in 2 ml of TFA (90%) and shaken for one hour. The solvent was removed in vacuo, and the product was lyophilized from water.

Yield: 60 mg (0.137 mmol) of lyophilized solid

HPLC: 25.61% B and 26.06% B (diastereomers)

2d) Bzls-d,l-hAla(2-Pyr-NO)-Ser (2-Boc-aminomethyl-5-chloro)benzylamide 60 mg of Bzls-d,l-hAla(2-Pyr)-Ser(tBu)-OH and 37 mg (0.137 mmol) of 2-Boc-amidomethyl-5-chlorobenzylamine were dissolved in 3 ml of DMF and, at 0° C., 71 mg of PyBop and sufficient DIEA to adjust a pH of 8.5 were added. The mixture was stirred at 0° C. for 20 min and at room temperature for a further 40 min. The solvent was then removed in vacuo, and the residue was taken up with ethyl acetate, washed 2 with saturated NaHCO₃ solution and 1 with saturated NaCl solution and dried over Na₂SO₄. The solvent was removed in vacuo.

Yield: 91 mg of yellow oil (crude product)
HPLC: 53.175% B and 53.81% B (diastereomers)

2) Bzls-d-hAla(2-Pyr-NO)-Ser (2-aminomethyl-5-chloro)-benzylamide 60 mg of 2d (crude product) were dissolved in 1 ml of TFA (90%) and shaken for 1 h. The solvent was removed in vacuo, and the mixture was purified by preparative RP-HPLC and lyophilized, the diastereomers having been separated. The d configuration of the final compound was determined via the inhibitory activity.

Yield: 10.5 mg of white solid
HPLC: 30.33% B
MS: calc. 589.18. found: 590.2 (M+H)$^+$ The following inhibitors were synthesized by an analogous strategy which has been described for the preparation of inhibitors 1 and 2. Well-known standard preparation processes of peptide chemistry were used for this. A modified synthetic strategy was used to synthesize inhibitors 9 and 27, which is described in detail. The last purification of all the inhibitors took place by preparative HPLC.

Inhibitor 3

Bzls-l,d-hAla(2-Pyr)-Ser (2-aminomethyl-5-chloro)-benzylamide TFA

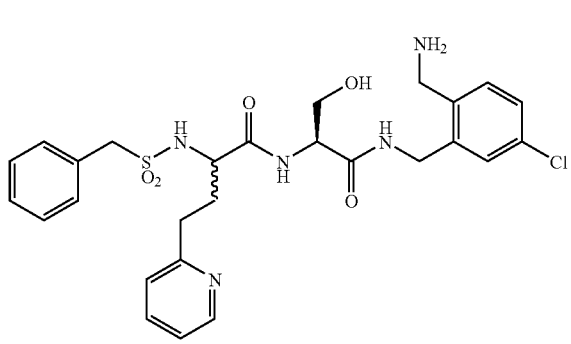

HPLC: 27.2% B (diastereomers not separated)
MS: calc.: 573.2. found: 574.2 [M+H]$^+$ Inhibitor 4

Props-l,d-hAla(2-Pyr-NO)-Gly (2-aminomethyl-5-chloro)-benzylamide TFA

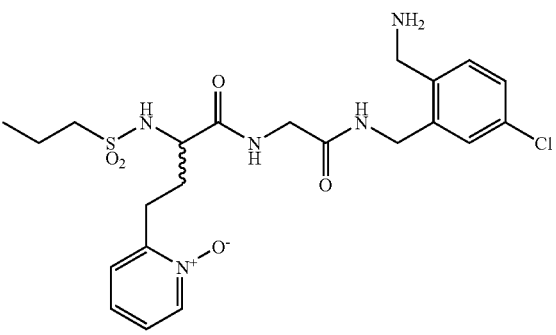

HPLC: 26.9% B
MS: calc.: 511.2. found: 512.2 [M+H]$^+$

Inhibitor 5

Bzls-l,d-hAla(2-Pyr-NO)-Glu(OMe) (2-aminomethyl-5-chloro)benzylamide TFA

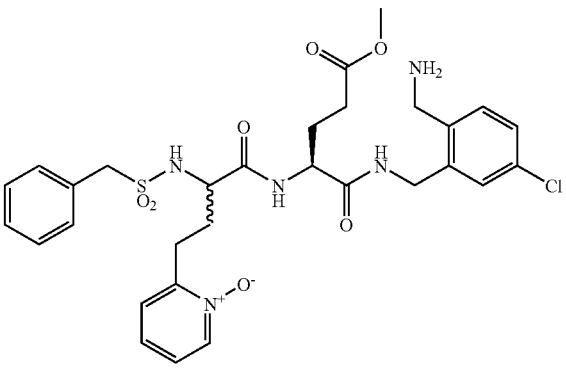

HPLC: diastereomers at 34.4 and 34.8% B
MS: calc.: 645.2 found: 646.3 [M+H]$^+$

Inhibitor 6

Bzls-l,d-hAla(2-Pyr-NO)-Glu (2-aminomethyl-5-chloro)-benzylamide TFA

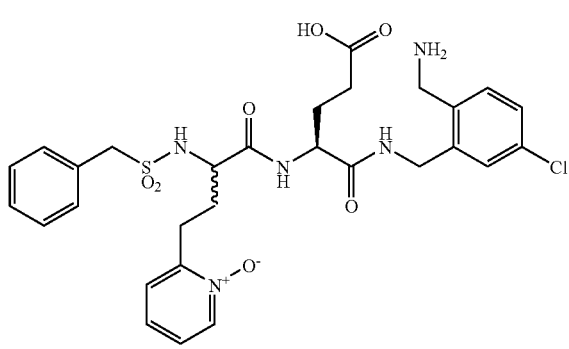

HPLC: 31.8% B (diastereomers not separated)
MS: calc.: 631.2. found: 632.3 [M+H]+

Inhibitor 7

Bzls-d-hAla(2-Pyr-NO)-Pro(2-aminomethyl-5-chloro)-benzylamide TFA

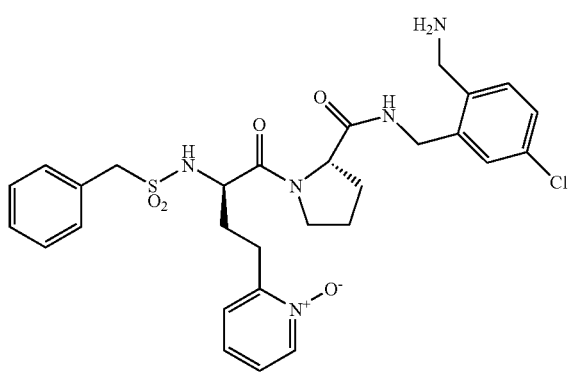

HPLC: 33.5% B (diastereomers)
MS: calc.: 599.2. found: 600.2 [M+H]+

Inhibitor 8

2-Hydroxy-4-Phenyl-butyl-Gly (2-aminomethyl-5-chloro)-benzylamide TFA

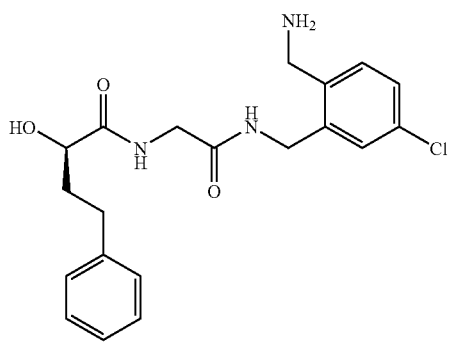

HPLC: 34.4% B, MS: calc.: 389.1. found: 390.1 [M+H]+

Inhibitor 9

H-l,d-N(CH$_2$—COOH)hAla(2-Pyr-NO)-Gly (2-aminomethyl-5-chloro)benzylamide 2 TFA

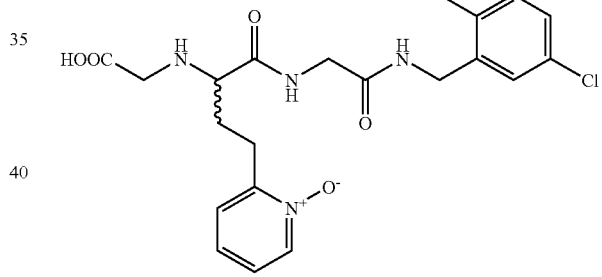

9a) Tfa-d,l-hAla(2-Pyr)-OH TFA

A solution of 1 equivalent of H-d,l-hAla(2-Pyr)-OH (0.5 g, 2.77 mmol) in TFA was cooled to −10° C. with an ice-salt mixture. Then, while stirring, 1.2 equivalents of trifluoroacetic anhydride (463 μl, 3.33 mmol) were added dropwise over the course of a few minutes. The cooling bath was removed and replaced by a water bath at 10° C. After 30 min, excess anhydride and TFA were concentrated in vacuo, and the residue (oil) was separated by preparative HPLC.
Yield: 894 mg (82%)
HPLC 15.5% B
MS: calc.: 276.07. found: 277.04 (M+H)+

9b) Tfa-d,l-hAla(2-Pyr)-Gly-OtBu

A solution of 1 equivalent of 9a (0.5 g, 1.28 mmol) and 1.05 equivalents of H-Gly-OtBu (225 mg, 1.34 mmol) in 6 ml of DMF was cooled to 0° C. while stirring in an ice bath. 2.7 equivalents of DIEA (600 μl, 3.47 mmol) and 1.05 equivalents of PyBOP (0.7 g, 1.34 mmol) were added to the cooled solution. After 15 min, the ice bath was removed and under the mixture was stirred at RT at pH 8-9 for 2 h. The solvent was then removed in vacuo, and the residue was taken up in ethyl acetate and washed 3 each with saturated $NaHCO_3$ solution NaCl solution. The ethyl acetate phase was dried over $Na_2SO_4$ and, after filtration, the solvent was concentrated in vacuo. The remaining oil was used without further working up for the next reaction.

Yield: 990 mg of crude product (oil), HPLC: 31.4% B

9c) Tfa-d,l-hAla(2-Pyr-NO)-Gly-OtBu

The crude product 9b was dissolved in DCM and, while stirring at RT, approx. 1.5 equivalents of mCPBA (70% pure, 475 mg, 1.92 mmol) were added. The HPLC check after 3 h showed starting material still present, and therefore a further 0.5 equivalent of mCPBA were introduced and the mixture stirred overnight. The solvent was concentrated in vacuo, the residue was taken up in 2M acetic acid, and the precipitate was filtered off. The filtrate was then adjusted to pH ~8.5 with aqueous $NH_3$ solution, and the solution was extracted 3 with EA. The ethyl acetate phase was dried over $Na_2SO_4$, and the solvent was concentrated in vacuo. The remaining oil was used without further working up for the next reaction.

Yield: 707 mg of crude product (oil)
HPLC: 36.0% B

9d) Tfa-d,l-hAla(2-Pyr-NO)-Gly-OH

The crude product 9c was mixed with 2 ml of 90% TFA and shaken at RT for 1 h, diluted with water and lyophilized. The remaining oil was used without further working up for the next reaction.

Yield: 596 mg of crude product (<100%)
HPLC 19.0% B
MS calc.: 349.09. found: 348.04 $(M-H)^-$

9e) Tfa-d,l-hAla(2-Pyr-NO)-Gly (2-Boc-amidomethyl-5-chloro)benzylamide

A solution of approx. 1 mmol of crude product 9d and 1 eq. of 2-(Boc-amidomethyl)-5-chloro)benzylamine (270 mg, 1 mmol) in 3 ml of DMF was cooled to 0° C. while stirring in an ice bath. 1 eq. of DIEA (175 μl, 1 mmol) and 1 eq. of PyBOP (523 mg, 1 mmol) were added to the cooled solution. After 15 min, the ice bath was removed and stirred at RT while monitoring the pH (pH 8-9) for 2 h. The solvent was then removed in vacuo, and the residue was taken up in ethyl acetate and washed 3 each with saturated $NaHCO_3$ and NaCl solutions. The ethyl acetate phase was dried over $Na_2SO_4$ and, after filtration, the solvent was concentrated in vacuo. The remaining crude product was purified by preparative HPLC.

Yield: 175 mg
HPLC 47.9% B

9f) H-d,l-hAla(2-Pyr-NO)-Gly (2-Boc-amidomethyl-5-chloro)benzylamide HCl

A solution of 9e (175 mg, 0.3 mmol) in 1 ml of dioxane and 1 ml of 1N NaOH was stirred at 40° C. for 3 h. It was then neutralized with 1N HCl, the solvent was concentrated in a rotary evaporator, and the residue was lyophilized. The remaining crude product was used without further working up for the next reaction.

HPLC 17.7% B
MS: calc.: 505.21. found: 506.1 $(M+H)^+$

9g) H-d,l-N($CH_2$—COOH)-hAla(2-Pyr-NO)-Gly (2-Boc-amidomethyl-5-chloro)benzylamide TFA 1.1 equivalents of $K_2CO_3$ (45 mg, 0.33 mmol) and 1.1 equivalents of ethyl acetate bromoacetate (55 mg, 0.33 mmol) were added to a solution of the crude product 9f in 5 ml of THF, and the mixture was stirred at RT for 24 h. The precipitate was filtered off and the solvent was concentrated in vacuo. The residue was then taken up in 2 ml of dioxane and stirred with 2 ml of 1N NaOH at RT for 2 h. The mixture was then neutralized with 1N HCl, the solvent was concentrated in vacuo, and the residue was purified by preparative HPLC.

Yield: 86 mg (53%)
HPLC 36.9% B
MS: calc.: 563.2. found: 564.1 $(M+H)^+$

9h) H-d,l-N($CH_2$—COOH)-hAla(2-Pyr-NO)-Gly (2-Boc-amidomethyl-5-chloro)benzylamide 2 TFA 86 mg (0.13 mmol) of 9g were mixed with 1 ml of 90% TFA and shaken at RT for 1 h and then lyophilized from $H_2O$. The residue was purified by preparative HPLC.

Yield: 61 mg (69%)
$C_{25}H_{26}ClF_6N_5O_9$: HPLC 17.5% B
MS: calc.: 463.2. found: 564.2 $(M+H)^+$

Inhibitor 10

Bzls-d-hAla(2-Pyr-NO)-Ala (2-aminomethyl-5-chloro)-benzylamide TFA (Preparation in Analogy to Inhibitor 1 Using H-Ala-OtBu for Step h)

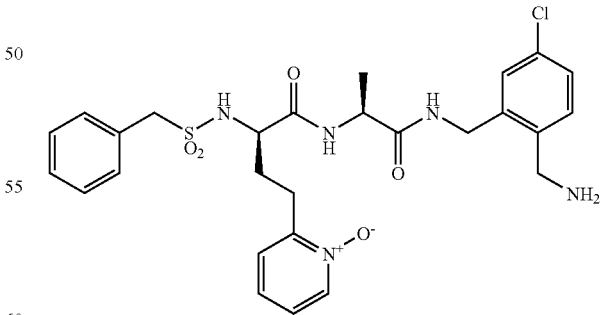

HPLC: 31.8% B, MS: calc.: 573.18. found: 574.2 $[M+H]^+$

Inhibitor 11

Bzls-d-hAla(2-Pyr-NO)-Glu(OMe) (2-aminomethyl-5-chloro)benzylamide TFA (Preparation in Analogy to Inhibitor 5 and Separation of the Diastereomers in the Last Step by Preparative HPLC)

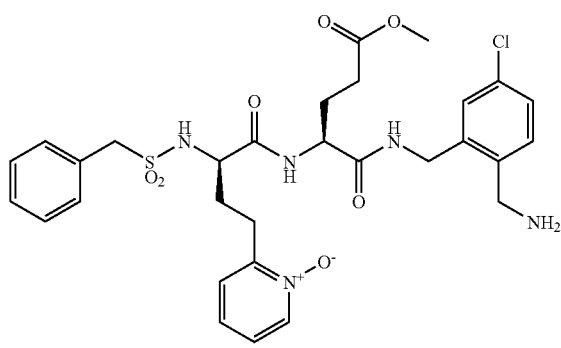

HPLC: 34.4% B, MS: calc.: 645.2. found: 646.3 [M+H]$^+$

Inhibitor 12

Bzls-d-hAla(2-Pyr-NO)-Dap(2-aminomethyl-5-chloro)-benzylamide 2 TFA (Preparation in Analogy to Inhibitor 1 Using H-Dap(Boc)-OMe for Step h and Hydrolysis of the Methyl Ester with LiOH in Step j)

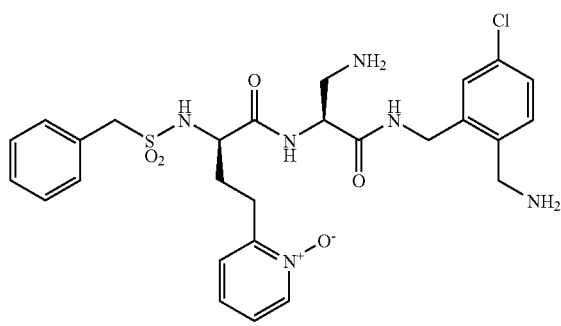

HPLC: 28.4% B, MS: calc.: 588.19. found: 589.2 [M+H]$^+$

Inhibitor 13

(4-MeOOC—CH$_2$)-Bzls-d/l-hAla (2-Pyr-NO)-Gly (2-amino-methyl-5-chloro)benzylamide TFA (Preparation in Analogy to Inhibitor 1 Using (4-MeOOC)-Bzls-d/l-hAla(2-Pyr)-OH for Step h)

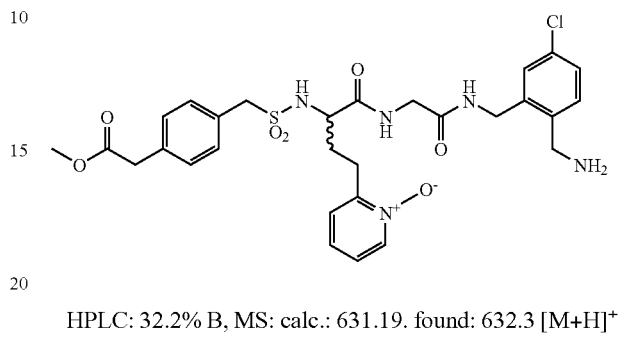

HPLC: 32.2% B, MS: calc.: 631.19. found: 632.3 [M+H]$^+$

Inhibitor 14

(4-HOOC—CH$_2$)-Bzls-d/l-hAla(2-Pyr-NO)-Gly (2-amino-methyl-5-chloro)benzylamide TFA (Preparation from Inhibitor 13 by Hydrolysis with LiOH in the Last Step)

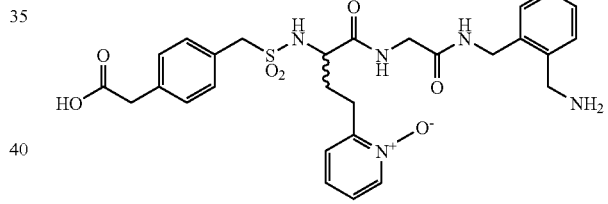

HPLC: 28.2% B, MS: calc.: 617.17. found: 618.3 [M+H]$^+$

Inhibitor 15

(4-HOOC—CH$_2$)-Bzls-d/l-hAla(2-Pyr)-Gly (2-aminomethyl-5-chloro)benzylamide TFA (Preparation in Analogy to Inhibitor 14 without Oxidation of the Pyridyl Nitrogen)

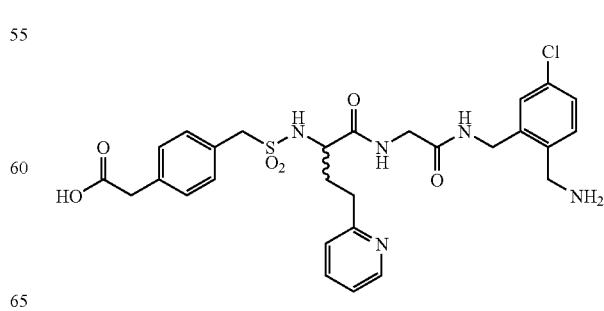

HPLC: 25.6% B, MS: calc.: 601.18. found: 602.3 [M+H]$^+$

Inhibitor 16

(4-MeOOC—CH$_2$)-Bzls-d-hAla(2-Pyr-NO)-Ser (2-aminomethyl-5-chloro)benzylamide TFA (Preparation in Analogy to Inhibitor 2 Using (4-MeOOC—CH$_2$)-Bzls-d/l-hAla(2-Pyr)-OH for Step a, the Diastereomers were Separated in the Last Step by Preparative HPLC)

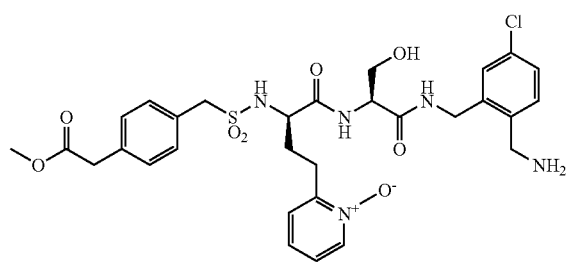

HPLC: 24.9% B, MS: calc.: 631.19. found: 632.2 [M+H]$^+$

Inhibitor 17

(4-HOOC—CH$_2$)-Bzls-d-hAla(2-Pyr-NO)-Ser (2-aminomethyl-5-chloro)benzylamide TFA (Preparation from Inhibitor 16 by Hydrolysis with LiOH in the Last Step and Purification by Preparative HPLC)

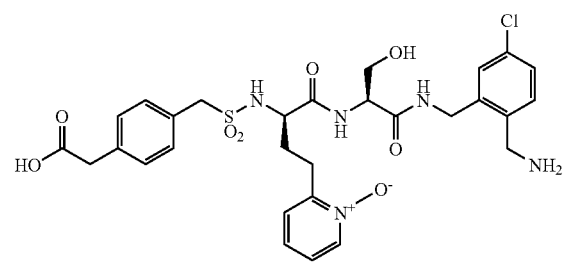

HPLC: 27.4% B, MS: calc.: 647.18. found: 648.3 [M+H]$^+$

Inhibitor 18

(4-MeOOC—CH$_2$)-Bzls-d/l-hAla (2-Pyr)-Ser (2-aminomethyl-5-chloro)benzylamide 2 TFA (Preparation in Analogy to Inhibitor 16 without Oxidation of the Pyridyl Nitrogen)

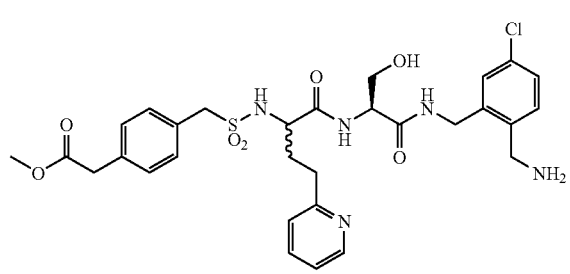

HPLC: 28.5% B, MS: calc.: 645.2. found: 646.3 [M+H]$^+$

Inhibitor 19

(4-HOOC—CH$_2$)-Bzls-d-hAla(2-Pyr)-Ser (2-aminomethyl-5-chloro)benzylamide TFA (Preparation from Inhibitor 18 by Hydrolysis with LiOH in the Last Step and Separation of the Diastereomers by Preparative HPLC)

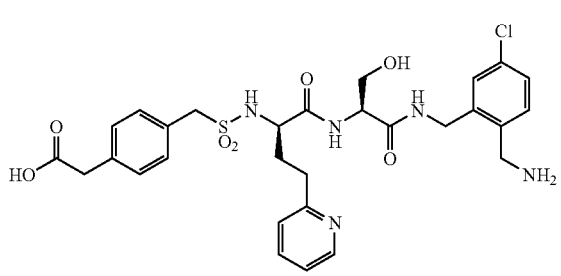

HPLC: 24.9% B, MS: calc.: 631.19. found: 632.3 [M+H]$^+$

Inhibitor 20

(4-MeOOC)-Bzls-d/l-hAla(2-Pyr-NO)-Gly (2-aminomethyl-5-chloro)benzylamide TFA (Preparation in Analogy to Inhibitor 1 Using (4-MeOOC)-Bzls-d/l-hAla(2-Pyr)-OH for Step h)

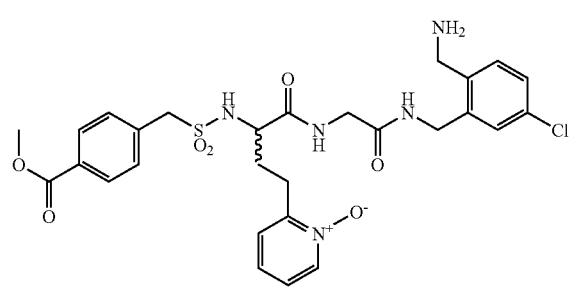

HPLC: 32.16% B, MS: calc.: 617.17. found: 618.2 [M+H]$^+$

Inhibitor 21

(4-HOOC)-Bzls-d/l-hAla(2-Pyr-NO)-Gly (2-aminomethyl-5-chloro)benzylamide TFA (Preparation from Inhibitor 20 by Hydrolysis with LiOH in the Last Step)

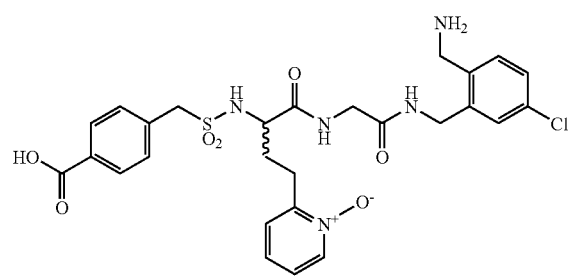

HPLC: 27.13% B, MS: calc.: 603.16. found: 604.2 [M+H]$^+$

Inhibitor 22

(4-MeOOC)-Bzls-d/l-hAla(2-Pyr)-Gly (2-aminomethyl-5-chloro)benzylamide 2 TFA (Preparation in Analogy to Inhibitor 20 without Oxidation of the Pyridyl Nitrogen)

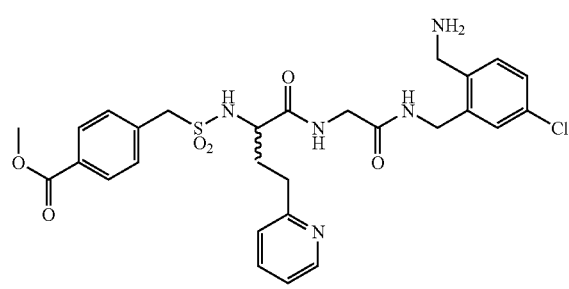

HPLC: 28.96% B, MS: calc.: 601.18. found: 602.2 [M+H]$^+$

Inhibitor 23

(4-HOOC)-Bzls-d/l-hAla(2-Pyr)-Gly (2-aminomethyl-5-chloro)benzylamide 2 TFA (Preparation from Inhibitor 22 by Hydrolysis with LiOH)

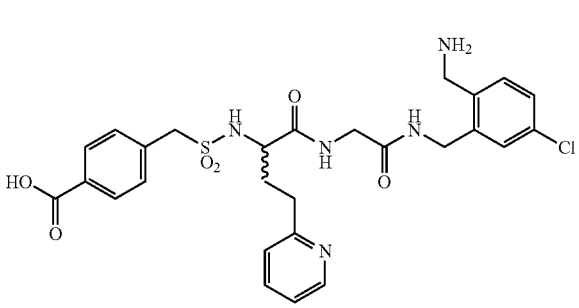

HPLC: 24.58% B, MS: calc.: 587.16. found: 588.2 [M+H]$^+$

Inhibitor 24

(4-MeOOC)-Bzls-d/l-hAla(2-Pyr-NO)-Ser (2-aminomethyl-5-chloro)benzylamide TFA (Preparation in Analogy to Inhibitor 2 Using (4-MeOOC)-Bzls-d/l-hAla(2-Pyr)-OH for step a)

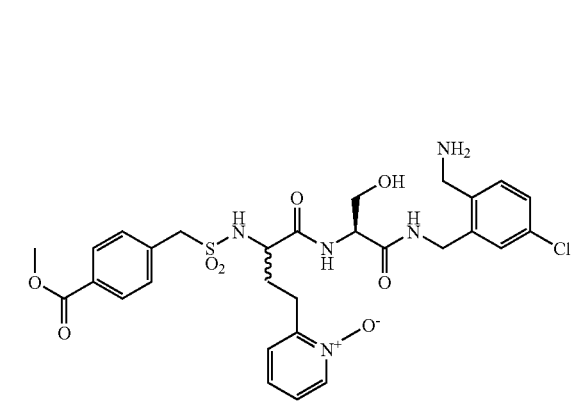

HPLC: 31.36% B, MS: calc.: 647.18. found: 648.2 [M+H]$^+$

Inhibitor 25

3-Pyridyl (NO)—CH$_2$—SO$_2$-d/l-hAla (2-Pyr-NO)-Gly (2-aminomethyl-5-chloro)benzylamide TFA (Preparation in Analogy to Inhibitor 1 Using 3-pyridyl-CH$_2$—SO$_2$-d/l-hAla(2-Pyr)-OH for Step h)

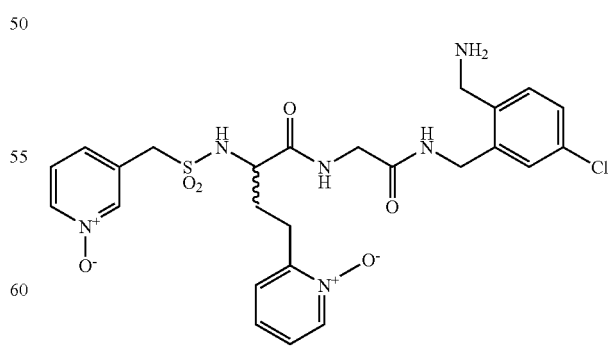

HPLC: 20.7% B, MS: calc.: 576.16. found: 577.2 [M+H]$^+$

Inhibitor 26

3-Pyridyl-CH$_2$—SO$_2$-d/l-hAla (2-Pyr)-Gly (2-aminomethyl-5-chloro)benzylamide 3 TFA (Preparation in Analogy to Inhibitor 25 without Oxidation of the Pyridyl Nitrogens)

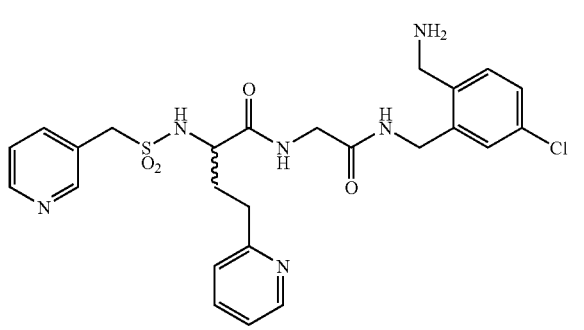

HPLC: 17.8% B, MS: calc.: 544.17. found: 545.2 [M+H]$^+$

Inhibitor 27

HOOC—CH$_2$—SO$_2$-d-hAla (2-Pyr-NO)-Pro (2-aminomethyl-5-chloro)benzylamide TFA

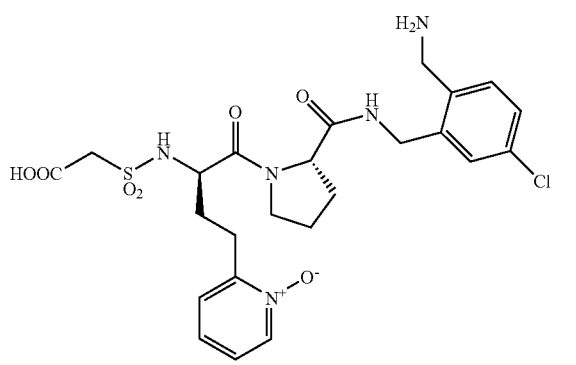

27a) Isopropyl Chlorosulfonacetate (Tetrahedron Lett. 2000, 41, 6743)

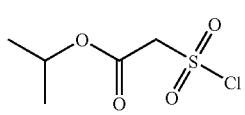

1.166 g (6.3 mmol) of commercially available methyl chlorosulfonacetate (Aldrich) were dissolved in 4 ml of dry diethyl ether and, at 0° C., 485 µl (6.3 mmol) of isopropanol were added. After stirring at RT for 2 h, the solvent was concentrated in vacuo and the residue was used without further working up for the next step.

27b) iPr-OOC—CH$_2$—SO$_2$-d/l-hAla(2-Pyr)-OH HCl

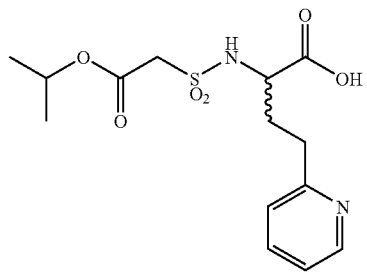

500 mg (2.77 mmol) of H-d,l-hAla(2-Pyr)-OH (1b) were suspended in 60 ml of dry DCM and, after addition of 830 µl (8.58 mmol) of TMS-Cl (Merck) and 1.5 ml (8.58 mmol) of DIEA (Fluka), heated under reflux for one hour. The now completely clear mixture was then cooled to 0° C., and 615 mg (3.05 mmol) of 11a and 530 µl (3.05 mmol) of DIEA were added. The pH was adjusted to 7.5-8 with additional DIEA and stirred at RT for a further 1.5 hours. The solvent was removed in vacuo, and the residue was taken up in 40 ml of water and washed 3 with a little ethyl acetate, and the aqueous phase was lyophilized.

Yield: 2.3 g of crude product with salts
HPLC: 21.2% B
MS: calc.: 344.1. found: 345.1 (M+H)$^+$

27c) iPr-OOC—CH$_2$—SO$_2$-d/l-hAla(2-Pyr)-Pro-OtBu TFA

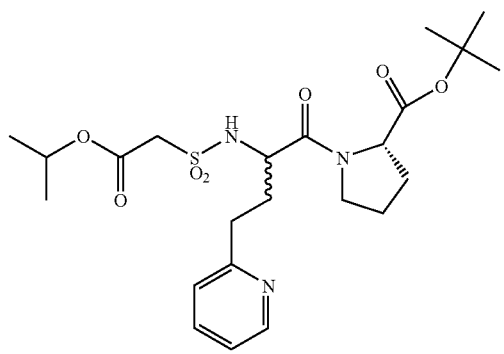

2.04 g (crude product, approx. 2.42 mmol) of 11b and 415 mg (2.42 mmol) of H-Pro-OtBu (Bachem) were dissolved in 15 ml of DMF and, at 0° C., 1.262 g (2.42 mmol) of PyBop and 422 µl (2.42 mmol) of DIEA were added. The pH was adjusted to approx. 8-9 by adding DIEA. The mixture was stirred at 0° C. for 15 min and at RT for a further 2 h. The solvent was then removed in vacuo, and the residue was taken up with ethyl acetate, washed 2 with saturated NaHCO$_3$ solution, 1 with saturated NaCl solution and dried over Na$_2$SO$_4$. The solvent was removed in vacuo, and the residue (oil) was separated by preparative RP-HPLC.

Yield: 410 mg of oil
HPLC: 38.0% B and 39.5% B (diastereomers)
MS: calc.: 497.2. found: 498.1 (M+H)$^+$ 27d) iPr-OOC—CH₂—SO₂-d/l-hAla(2-Pyr-NO)-Pro-OtBu 27f) iPr-OOC—CH₂—SO₂-d-hAla(2-Pyr-NO)-Pro (2-Boc-amidomethyl-5-chloro)benzylamide

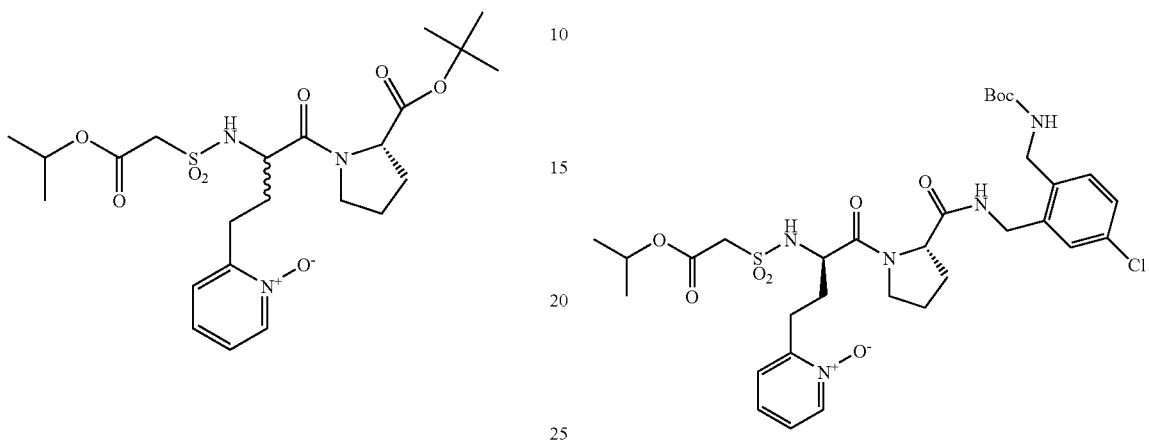

410 mg (0.67 mmol) of 11c were dissolved in 100 ml of dry DCM and, at 0° C., 500 mg (2.02 mmol) of mCPBA (70%) were added in portions and then stirred at RT for one hour. After one hour (HPLC checked), a further 190 mg (0.767 mmol) of mCPBA were added in portions. The solvent was removed in vacuo, and the residue was taken up with ethyl acetate, washed 2 with saturated NaHCO₃ solution, 1 with saturated NaCl solution and dried over Na₂SO₄. The solvent was removed in vacuo.

Yield: 800 mg of yellowish oil (crude product).

HPLC: 43.3% B and 45.0% B (diastereomers)

27e) iPr-OOC—CH₂—SO₂-d-hAla(2-Pyr-NO)-Pro-OH

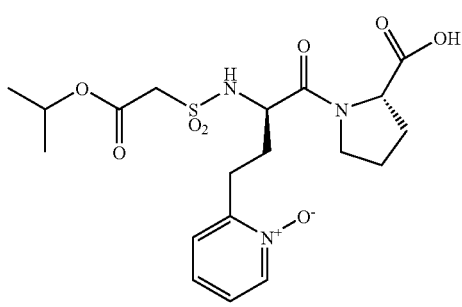

800 mg of 11d (crude product) were dissolved in 4 ml of TFA (90%) and shaken at RT for one hour. The solvent was removed in vacuo, and the diastereomers were separated by preparative HPLC.

Yield: 70 mg of pure diastereomer (oil)

HPLC: 29.1% B 70 mg (0.153 mmol) of 11e and 42 mg (0.153 mmol) of H-Amb(2-Boc-amidomethyl,5-Cl) (Nelson, T. D. et al., J. Org. Chem. 69 3620 (2004)) were dissolved in 5 ml of DMF and, at 0° C., 79 mg (0.153 mmol) of PyBop and 26 µl (0.153 mmol) of DIEA were added. The pH was adjusted to 8-9 by further addition of DIEA. The mixture was stirred at 0° C. for 15 min and at room temperature for a further hour. The solvent was then removed in vacuo, and the residue was taken up with ethyl acetate, washed 2 with saturated NaHCO₃ solution, 1 with saturated NaCl solution and dried over Na₂SO₄.

Yield: 145 mg of amorphous solid.

HPLC: 41.59% B

27g) HOOC-Me-SO₂-d-hAla(2-Pyr-NO)-Pro (2-aminomethyl-5-chloro)benzylamide TFA 145 mg of 11f (crude product) were dissolved in 1 ml of TFA (90%) and shaken at room temperature for 1 h. The solvent was removed in vacuo, and the residue was taken up with 3 ml of 1M LiOH and 3 ml of MeOH and shaken at room temperature for one hour. The solution was neutralized with 10% TFA, and the solvent was removed in vacuo. The residue was separated by preparative RP-HPLC, and the product was lyophilized.

Yield: 53 mg (white solid).

HPLC: 24.48% B, MS: calc.: 567.16. found: 568.2 [M+H]⁺

Inhibitor 28 iPr-OOC—CH₂—SO₂-d/l-hAla (2-Pyr-NO)-Gly
(2-aminomethyl-5-chloro)benzylamide TFA (Preparation in Analogy to Inhibitor 27 without Final Hydrolysis of the Isopropyl Ester Using H-Gly-OtBu for Step c)

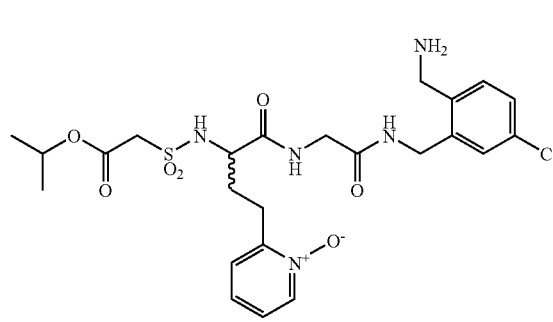

HPLC: 29.7% B, MS: calc.: 569.17. found: 570.2 [M+H]⁺

Inhibitor 29

HOOC—CH₂—SO₂-d/l-hAla (2-Pyr-NO)-Gly
(2-aminomethyl-5-chloro)benzylamide TFA (Preparation from Inhibitor 28 by Hydrolysis with LiOH)

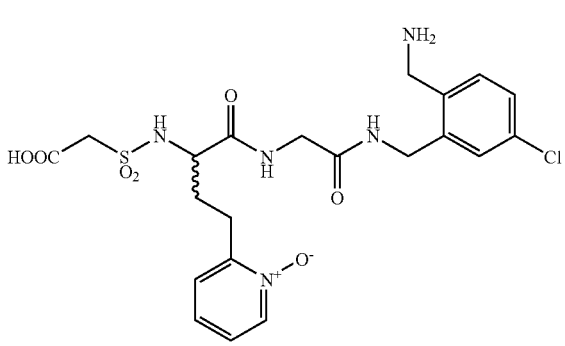

HPLC: 21.4% B, MS: calc.: 527.12. found: 528.3 [M+H]⁺

Inhibitor 30 iPr-OOC—CH₂—SO₂-d/l-hAla (2-Pyr)-Gly (2-aminomethyl-5-chloro)benzylamide 2 TFA (Preparation in Analogy to Inhibitor 28 without Oxidation of the Pyridyl Nitrogen)

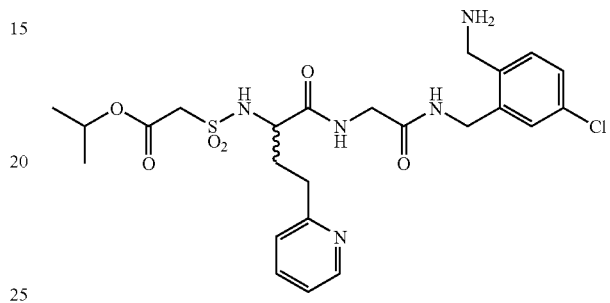

HPLC: 26.7% B, MS: calc.: 553.18. found: 554.3 [M+H]⁺

Inhibitor 31

Oxalyl-d/l-hAla(2-Pyr-NO)-Pro (2-aminomethyl-5-chloro)-benzylamide TFA (Preparation in Analogy to Inhibitor 2 Using methoxalyl-d/l-hAla (2-Pyr)-OH and H-Pro-OtBu for Step a and Hydrolyzing with LiOH in the Last Step)

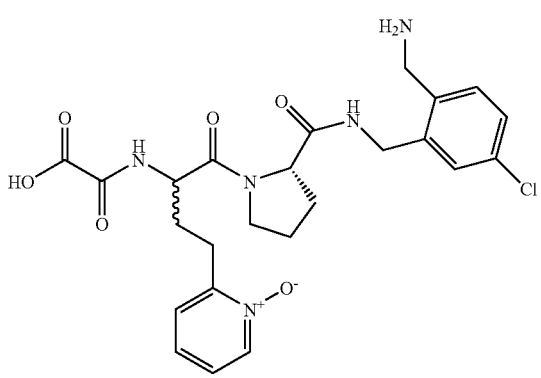

HPLC: 23.9% B, MS: calc.: 517.17. found: 518.2 [M+H]⁺

Inhibitor 32

Malonyl-d/l-hAla(2-Pyr-NO)-Gly (2-aminomethyl-5-chloro)benzylamide TFA (Preparation in Analogy to Inhibitor 2 Using ethoxymalonyl-d/l-hAla (2-Pyr)-OH and H-Gly-OtBu for Step a and Hydrolyzing with LiOH in the Last Step)

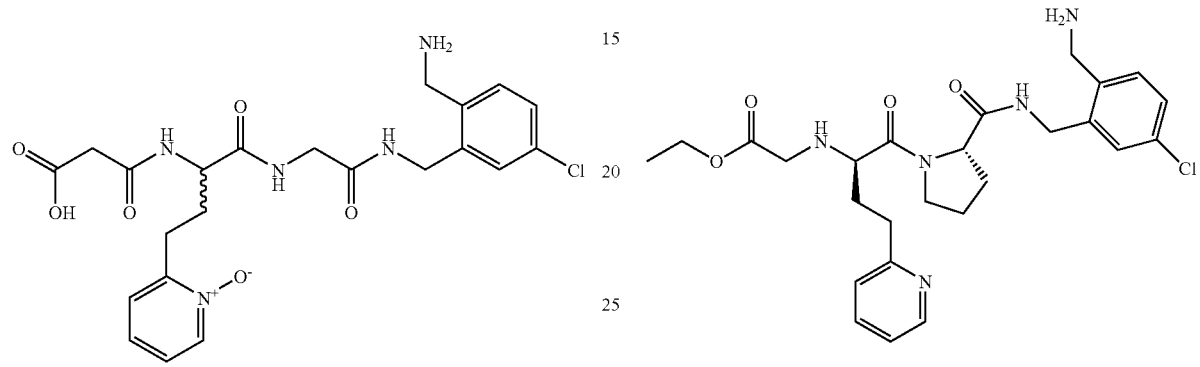

HPLC: 20.4% B, MS: calc.: 491.16. found: 492.1 [M+H]$^+$

Inhibitor 33

H-d-N(CH$_2$—COOEt)hAla(2-Pyr-NO)-Pro (2-aminomethyl-5-chloro)benzylamide 2 TFA (Preparation in Analogy to Inhibitor 9 Using H-Pro-OtBu for Step b, the Diastereomers were Separated in the Last Step by Preparative HPLC)

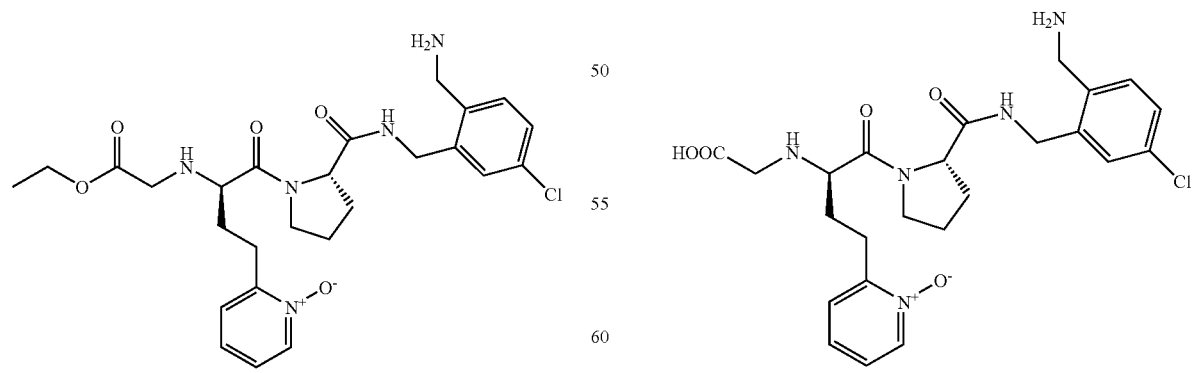

HPLC: 23.23% B, MS: calc.: 531.22. found: 532.3 [M+H]$^+$

Inhibitor 34

H-d-N(CH$_2$—COOEt)hAla(2-Pyr)-Pro (2-aminomethyl-5-chloro)benzylamide 3 TFA (Preparation in Analogy to Inhibitor 33 without Oxidation of the Pyridyl Nitrogen).

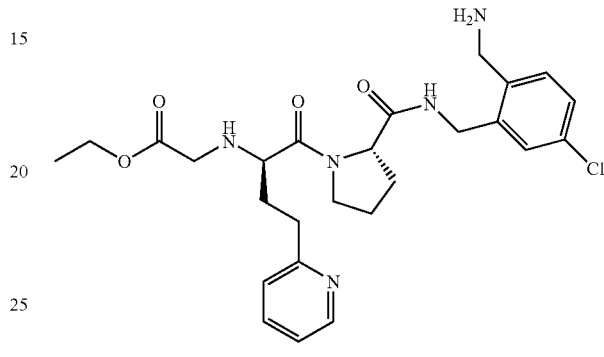

HPLC: 21.7% B, MS: calc.: 515.23. found: 516.2 [M+H]$^+$

Inhibitor 35

H-d-N(CH$_2$—COOH)hAla(2-Pyr-NO)-Pro (2-aminomethyl-5-chloro)benzylamide 2 TFA (Preparation from Inhibitor 33 by Hydrolysis with LiOH in the Last Step)

HPLC: 20.36% B, MS: calc.: 503.19. found: 504.3 [M+H]$^+$

Inhibitor 36

H-d-N(CH$_2$—COOH)hAla(2-Pyr)-Pro (2-aminomethyl-5-chloro)benzylamide 3 TFA (Preparation in Analogy to Inhibitor 35 without Oxidation of the Pyridyl Nitrogen).

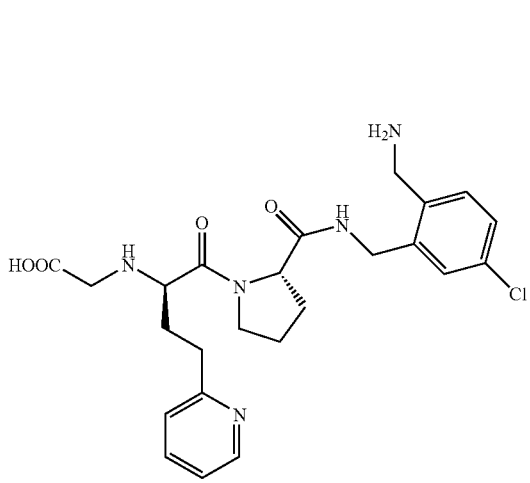

HPLC: 18.0% B, MS: calc.: 487.19. found: 488.2 [M+H]$^+$

Inhibitor 37

H-d-N(CH$_2$—COO-Hexyl)hAla (2-Pyr-NO)-Pro (2-aminomethyl-5-chloro)benzylamide 2 TFA (Synthesis in Analogy to Inhibitor 9 Using Hexyl Bromoacetate for Step g)

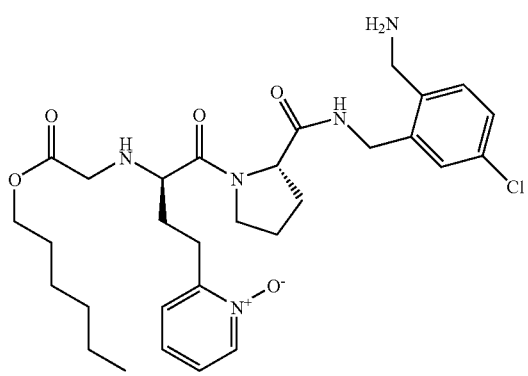

HPLC: 35.55% B, MS: calc.: 587.29. found: 588.4 [M+H]$^+$

Inhibitor 38

H-d-N(CH$_2$—COO—Cyclohexyl)hAla(2-Pyr-NO)-Pro (2-aminomethyl-5-chloro)benzylamide 2 TFA (Synthesis in Analogy to Inhibitor 9 Using Cyclohexyl Bromoacetate for Step g)

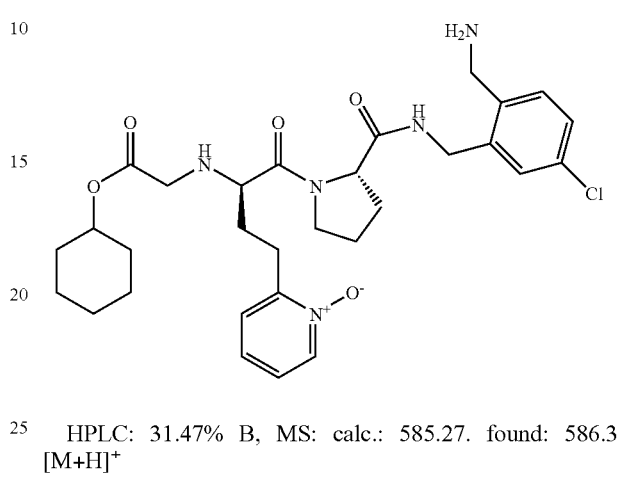

HPLC: 31.47% B, MS: calc.: 585.27. found: 586.3 [M+H]$^+$

Inhibitor 39

H-d-N(CH$_2$—COOH)hTyr-Pro (2-aminomethyl-5-chloro)-benzylamide 2 TFA (Preparation in Analogy to Inhibitor 9 Using Tfa-d-hTyr(tBu)-OH and H-Pro-OtBu for Step b)

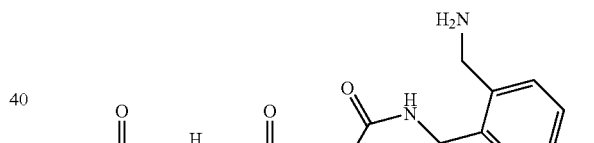

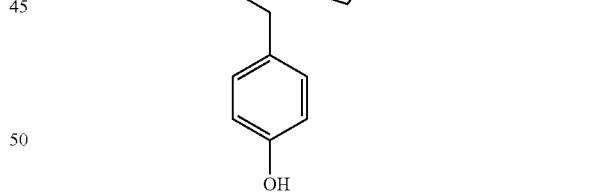

HPLC: 25.2% B, MS: calc.: 502.2. found: 503.2 [M+H]$^+$

EXAMPLE 2

Enzyme Kinetic Investigations to Determine the Inhibitory Effect

The inhibitory effect of the inhibitors for factor Xa, thrombin and plasmin were estimated using specific synthetic chromogenic substrates. The absorption was determined at 405 nm using a microplate reader (iEMS reader MF 1401, LAB-SYSTEMS, Helsinki, Finnland), and the K$_i$ values were calculated by Dixon's linear regression with the aid of a computer program. Determination of K$_i$ values >2 nM took place in Tris buffer (0.05M Tris; 0.9% NaCl; 5% ethanol; pH 8.0) on microtiter plates at 25° C. The inhibitor was dissolved in Tris buffer, the substrates (all Pentapharm Ltd., Basel, CH) in water. 25 μl of substrate solution and 50 μl of enzyme solution were added to 200 μl of inhibitor solution, and the reaction was stopped after 3-5 min by adding 25 μl of 50% acetic acid (Stürzebecher, J. et al., J. Med. Chem. 40, 3091 (1997)). For $K_i$ values <2.0 nM for FXa, the measurements were repeated with a reduced enzyme concentration (100 pM in the mixture) in acrylic cuvettes in a Specord M 400 UV-Vis spectrophotometer (Carl Zeiss, Jena). Three different substrate concentrations and five different inhibitor concentrations were measured in each case. The calculated $K_i$ values correspond to the averages from at least two individual determinations whose individual values do not differ by more than 25%.

The following enzymes and substrates were used for the measurements:
Human factor Xa (Enzyme Research Lab., purchased from Haemochrom Diagnostica GmbH, Essen)
Enzyme content: 0.67 μg/ml
Substrate: $CH_3OCO$-D-Cha-Gly-Arg-pNA (Pefachrome Xa),
concentration: 4, 2 and 1 mM; reaction time: 4 min
Thrombin (bovine)
Enzyme content: 2.5 IE/ml (in 0.9% NaCl with 1% HSA)
Substrate: $CH_3SO_2$-D-HHT-Gly-Arg-pNA (Pefachrome tPA),
concentration: 2, 1 and 0.5 mM; reaction time: 3 min
Human plasmin (CHROMOGENIX, Milano, Italy)
Enzyme content: 500 μg/ml enzyme (in 0.9% NaCl with 25% glycerol)
Substrate: Tos-Gly-Pro-Lys-pNA (Chromozym PL), concentration: 2, 1 and 0.67 mM; reaction time: 3 min

TABLE 1

Inhibition of FXa, thrombin and plasmin by various inhibitors

| Inhibitor | $K_i$ (nM) | | |
|---|---|---|---|
| | FXa | Thrombin | Plasmin |
| 1 | 0.095 | 170 | 600000 |
| 2 | 0.059 | 860 | 350000 |
| 3 | 0.25 | 260 | 350000 |
| 4 | 3.4 | 2630 | 280000 |
| 5 | 0.43 | 350 | 130000 |
| 6 | 0.52 | 20500 | 400000 |
| 7 | 0.049 | 0.56 | 8470 |
| 8 | 2200 | 1600 | 540000 |
| 9 | 16 | 125000 | >1000000 |
| 10 | 0.033 | 170 | 85000 |
| 11 | 0.24 | 180 | 78000 |
| 12 | 0.54 | 750 | 2300 |
| 13 | 0.35 | 1005 | 200000 |
| 14 | 0.36 | 930 | >1000000 |
| 15 | 0.68 | 140 | >1000000 |
| 16 | 0.14 | 800 | >1000000 |
| 17 | 0.18 | 540 | >1000000 |
| 18 | 0.67 | 430 | >1000000 |
| 19 | 0.78 | 210 | 100000 |
| 20 | 0.3 | 360 | 140000 |
| 21 | 4.1 | 1300 | 130000 |
| 22 | 1.05 | 100 | 98000 |
| 23 | 11 | 330 | 140000 |
| 24 | 0.48 | 930 | 160000 |
| 25 | 1.4 | 2500 | >1000000 |
| 26 | 0.34 | 140 | 210000 |
| 27 | 0.08 | 22 | 98000 |
| 28 | 7.6 | 1600 | 305000 |
| 29 | 1.6 | 8300 | >1000000 |
| 30 | 2.1 | 66 | 290000 |
| 31 | 0.88 | 43 | 80000 |

TABLE 1-continued

Inhibition of FXa, thrombin and plasmin by various inhibitors

| Inhibitor | $K_i$ (nM) | | |
|---|---|---|---|
| | FXa | Thrombin | Plasmin |
| 32 | 65 | 140 | n.d. |
| 33 | 0.4 | 4.9 | 240000 |
| 34 | 2.9 | 3.8 | n.d. |
| 35 | 0.4 | 17.2 | 100000 |
| 36 | 1.5 | 3.5 | n.d. |
| 37 | 0.92 | n.d. | n.d. |
| 38 | 1.01 | n.d. | n.d. |
| 39 | 8.3 | n.d. | n.d. | n.d. = not determined

EXAMPLE 3

Determination of the Inhibitory Effect of the Inhibitors on the Prothrombinase Complex (PTC) and Coagulation in Human Plasma (TT, aPTT, PT)

The $IC_{50}$ Values for Inhibition of the Prothrombinase complex were estimated using a specific chromogenic substrate. The absorption was determined using a microplate reader (see above) at 405 nm and 37° C. The prothrombinase complex was prepared by cautiously mixing 250 μl of cephalin (Cephalin lyophilizate from PTT reagent, Roche Diagnostics, Mannheim; dissolved in 5 ml of Tris buffer A (0.05 M Tris; 0.9% NaCl; pH 7.5)), 50 μl of 0.5M $CaCl_2$, 25 μl of factor Xa (human, Haemochrom Diagnostica GmbH, Essen; 0.16 μg/ml), 80 μl of factor Va (human, American Diagnostica, Greenwich, USA; 52 μg/ml) and 1845 μl of Tris buffer B (0.05 M Tris; 0.9% NaCl; 0.1% PEG 6000; pH 7.5) on ice and substituted incubating at 0° C. for 30 min. The inhibitor was dissolved in Tris buffer B with 5% ethanol. 25 μl of inhibitor solution were incubated with 45 μl of prothrombinase complex at RT for 5 min. Then 30 μl of prothrombin (human, Haemochrom Diagnostica GmbH, Essen; 29 μg/ml) were added and, after incubation at 37° C. for 10 min, the reaction was stopped by adding 150 μl of 0.083 mM EDTA in buffer B.

The activity of the thrombin formed was determined chromogenically by adding 50 μl of substrate (H-D-Phe-Pip-Arg-pNA HCl, S-2238, Haemochrom Diagnostica GmbH, Essen; 0.6 mM) and 200 μl of EDTA in Tris buffer B to 25 μl of the incubation mixture.

The $IC_{50}$, i.e. the concentration of inhibitor which causes 50% inhibition of the formation of thrombin, was determined graphically. In order to prevent simulation of inhibition of the prothrombinase complex through direct thrombin inhibition, the direct inhibition of the generated thrombin was also measured (by adding 25 μl of Tris buffer B with the highest inhibitor concentration after stopping with EDTA). Where the direct inhibition of the thrombin formed was >7%, no $IC_{50}$ has been indicated. Five different inhibitor concentrations were measured in each case. The calculated $IC_{50}$ values correspond to the averages from at least three individual determinations whose individual values do not differ by more than 25%.

The clotting times were determined using human citrated plasma which was centrifuged at 3000 rpm for 10 min. The measurements were carried out at 37° C. with the Thrombotrack coagulometer (Immuno GmbH, Heidelberg).

The $IC_{200}$ was calculated from the dependence of the clotting time on the concentration of the inhibitor. This gives the concentration of inhibitor which brings about a doubling of the clotting time. The calculated $IC_{200}$ values correspond to the averages from at least three individual determinations whose individual values do not differ by more than 25%.

Thrombin Time (TT)

100 μl of human citrated plasma were mixed with 50 μl of inhibitor solution in NaCl (0.9%; 5% ethanol) and incubated at 37° C. for 2 min. The coagulation was started by adding 50 μl of thrombin (2.5 IU/ml in 0.9% NaCl with 1% HSA).

Prothrombin Time (PT)

50 μl of the inhibitor solution in $CaCl_2$ (0.025 M; 5% ethanol) were incubated with 50 μl of thromboplastin (Dade Diagnostika GmbH, Unterschleißheim) at 37° C. for 2 min. Coagulation was started by adding 50 μl of human citrated plasma.

Activated Partial Thromboplastin Time (aPTT)

50 μl of human citrated plasma were incubated with 50 μl of PTT reagent (Roche Diagnostics, Mannheim) at 37° C. for 3 min. Coagulation was started by adding 50 μl of $CaCl_2$ solution (0.025 M; 5% ethanol) containing the inhibitor.

TABLE 2

Inhibition of the prothrombinase complex (PTC) and anticoagulant activity in human plasma

| | PTC | $IC_{50}$ values (nM) for the anticoagulation | | |
|---|---|---|---|---|
| Inhibitor | $IC_{50}$ (nM) | TT | aPTT | PT |
| 1 | 0.48 | 500 | 160 | 140 |
| 2 | 0.51 | 1380 | 270 | 200 |
| 4 | n.d.* | 6500 | 600 | 450 |
| 5 | n.d. | 820 | 220 | 90 |
| 6 | n.d. | >100000 | 750 | 520 |
| 26 | n.d. | 600 | 170 | 350 |
| 27 | n.d. | 110 | 150 | 390 |
| 28 | n.d. | 4200 | 420 | 730 |
| 29 | n.d. | 71000 | 800 | 1300 |
| 31 | n.d. | 140 | 360 | 410 |
| 33 | n.d. | 100 | 180 | 470 |
| 35 | n.d. | 170 | 320 | 610 |

*n.d. = not determined.

The invention claimed is:

1. A compound of the formula I:

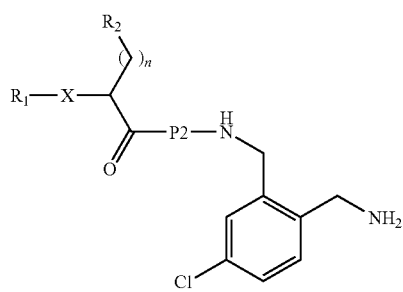

and pharmaceutically suitable salts of this compound, in which $XR_1$=—OH, —$OCH_2$—$COOR_4$, —$OSO_2$—$R_5$, —$OCOOR_5$, —OCO—$R_6$, —$NR_3CH_2$—$COOR_4$, —$NR_3SO_2$—$R_5$, —$NR_3COOR_5$, or —$NR_3CO$—$R_6$;

$R_3$=H or a branched or unbranched alkyl group having 1-6 C atoms, n=0, 1, 2, 3 or 4, $R_4$=H or a branched or unbranched alkyl group having 1-6 C atoms, $R_5$=a branched or unbranched alkyl group having 1-7 C atoms which is unsubstituted or substituted by $R_7$, or an aryl or heteroaryl group which is unsubstituted or substituted by $R_7$, or an aralkyl or heteroaralkyl group which is unsubstituted or substituted by $R_7$, or a cyclohexylmethyl group $R_7$=halogen, CN, $NHR_3$, NHCO—$R_3$, —$CH_2$—$NHR_3$, $NO_2$, $OR_3$, $SR_3$, —$COOR_4$ or —$CH_2$—$COOR_4$ and $R_3$ and $R_4$ as defined above $R_6$=a branched or unbranched alkyl group having 1-8 C atoms, which is unsubstituted or substituted by $R_7$, or cycloalkyl or a cyclohexylmethyl, but also —$COOR_4$, where $R_4$ is as defined above; and $R_6$ may also be substituted by $R_7$ which is as defined above, and $R_2$=a group selected from

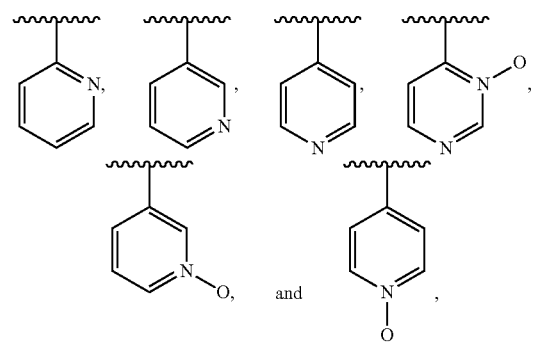

P2=any natural or unnatural α-amino acid, that is glycine or has the following structure

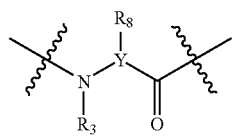

with $R_3$ as defined above,

Y=CH or N, and, in the case of $R_8$=H, may only be N, $R_8$=H or a branched or unbranched alkyl group having 1-8 C atoms, which is unsubstituted or substituted by $R_7$, or an aryl or heteroaryl group which is unsubstituted or substituted by $R_7$, or an aralkyl or heteroaralkyl group which is unsubstituted or substituted by $R_7$, or a cyclohexylmethyl group, and where $R_7$ is defined as described above, or P2=any α-azaimino acid of the following structure

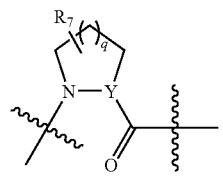

q=0, 1 or 2, and a carbon atom of the ring may be substituted by $R_7$ which is as defined above; and wherein P2 is not glycine alkylated on the nitrogen atom.

2. The compound as claimed in claim 1, wherein $XR_1$ is O—$CH_2$—COOH, O—$CH_2$—$COOCH_2CH_3$, O(benzylsulfonyl), O(methylsulfonyl), O(ethylsulfonyl), O(n-propylsulfonyl), O(n-butylsulfonyl), NR₃—CH₂—COOCH₂CH₃, NR₃(benzylsulfonyl), NR₃(methylsulfonyl), NR₃(ethylsulfonyl), NR₃(n-propylsulfonyl), or NR₃(n-butylsulfonyl).

3. The compound as claimed in claim 1, wherein the amino acid with X and R₂ has the following structure:

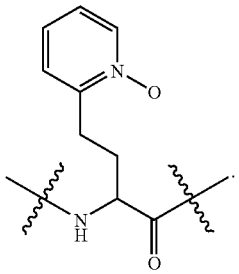

4. The compound as claimed in claim 1, wherein the amino or imino acid with X and R₂ is in the D configuration.

5. The compound as claimed in claim 1, wherein P2 is azaglycine, azaproline, serine, glutamic acid, ethyl glutamate, methyl glutamate, or α,β-diaminopropionic acid.

6. The compound as claimed in claim 1, wherein R₇ is an OH, an NH₂, a —COOH, a —COOCH₂CH₃, a —CH₂—COOH, or a —CH₂—COOCH₂CH₃ group.

7. The compound as claimed in claim 1, wherein XR₁=O—CH₂—COOR₄ or NR₃—CH₂—COOR₄, and n=2.

8. The compound as claimed in claim 1, wherein XR₁ is O—CH₂COOC₆H₁₁ or NR₃—CH₂COOC₆H₁₁, and/or P2 is alanine.

9. The compound as claimed in claim 1, wherein
XR₁=OH, O—CH₂—COOR₄, O—SO₂—R₅, O—COOR₅, OCO—R₆; NR₃—CH₂—COOR₄, NR₃—SO₂—R₅, NR₃—COOR₅ or NR₃CO—R₆;
R₃=H,
n=2
R₄=H or a branched or unbranched alkyl group having 1-6 C atoms,
R₅=a branched or unbranched alkyl group having 1-7 C atoms which is unsubstituted or substituted by R₇, or an aralkyl or heteroaralkyl group which is unsubstituted or substituted by R₇,
R₇=NHR₃, OR₃ or —COOR₄, and R₃ and R₄ are as described above
R₆=—COOR₄, where R₄ is as described above, and
P2=any natural or unnatural α-amino acid that is glycine or has the following structure

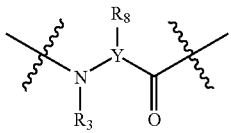

with
R₃ as defined above,
Y=CH or N, and, in the case of R₈=H, may only be N,
R₈=H or a branched or unbranched alkyl group having 1-8 C atoms, which is unsubstituted or substituted by R₇; and
wherein P2 is not glycine alkylated on the nitrogen atom.

10. The compound as claimed in claim 1, wherein
XR₁=NR₃—CH₂—COOR₄ or NR₃—SO₂—R₅,
R₃=H,
n=2
R₄=H or ethyl,
R₅=branched or unbranched alkyl group having 1-4 C atoms, or an aralkyl or heteroaralkyl group which is unsubstituted or substituted by R₇,
R₇=OR₃ or —COOR₄ and R₃ and R₄ as defined above
P2=any natural or unnatural α-amino acid that is glycine or has the following structure

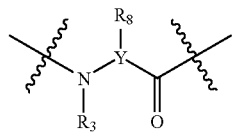

with
R₃ as defined above,
Y=CH or N and, in the case of R₈=H, may only be N,
R₈=H or a branched or unbranched alkyl group having 1-8 C atoms, which is unsubstituted or substituted by R₇; and
wherein P2 is not glycine alkylated on the nitrogen atom.

11. A method of inhibiting coagulation factor Xa, comprising administering to a patient in need thereof a compound of the general formula I:

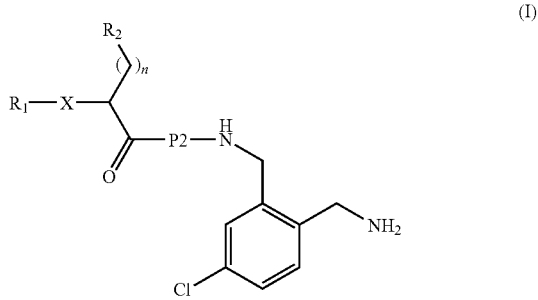

(I)

or pharmaceutically suitable salts of these compounds as inhibitors of coagulation factor Xa, where
XR₁=—OH, —OCH₂—COOR₄, —OSO₂—R₅, —OCOOR₅, —OCO—R₆—NR₃CH₂—COOR₄, —NR₃SO₂—R₅, —NR₃COOR₅, or —NR₃CO—R₆;
R₃ is H or a branched or unbranched alkyl group having 1-6 C atoms,
n=0, 1, 2, 3 or 4,
R₄=H or a branched or unbranched alkyl group having 1-6 C atoms,
R₅=a branched or unbranched alkyl group having 1-7 C atoms, which is unsubstituted or substituted by R₇, or R₅ is an aryl or heteroaryl group which is unsubstituted or substituted by R₇, or R₅ is an aralkyl or heteroaralkyl group which is unsubstituted or substituted by R₇, or a cyclohexylmethyl group
R₇=halogen, CN, NHR₃, NHCO—R₃, —CH₂—NHR₃, NO₂, OR₃, SR₃, —COOR₄ or —CH₂—COOR₄ and R₃ and R₄ as defined above
R₆=a branched or unbranched alkyl group having 1-8 C atoms, which is unsubstituted or substituted by R₇, or cycloalkyl or a cyclohexylmethyl, but also —COOR₄, where $R_4$ is as defined above; and $R_6$ may also be substituted by $R_7$ which is as defined above, and
$R_2$=a group selected from

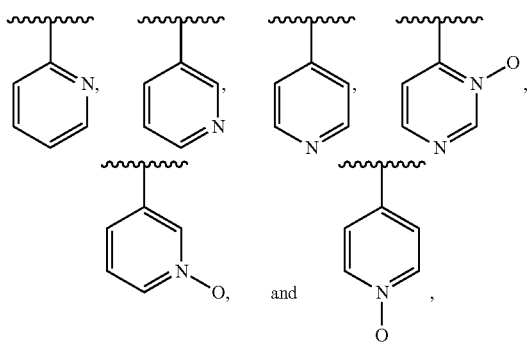

P2=any natural or unnatural α-amino acid or α-azaamino acid of the following structure

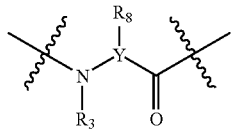

with
$R_3$ and $R_8$ as defined above, and
Y=CH or N, or
P2=any α-imino acid or α-azaimino acid of the following structures

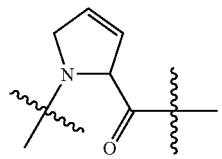

or

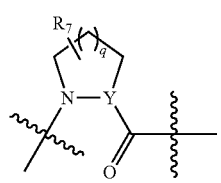

with $R_7$ and Y as defined above, and
q=0, 1 or 2, and one carbon atom of the ring may be substituted by $R_7$ which is as defined above.

12. The method as claimed in claim 11, wherein $XR_1$=O—$CH_2$—$COOR_4$ or $NR_3$—$CH_2$—$COOR_4$, and n=2.

13. The method according to claim 11, wherein $R_1$ is —$CH_2COOC_6H_{11}$ and/or P2 is an alanine.

14. The method as claimed in claim 11, wherein
$XR_1$=OH, O—$CH_2$—$COOR_4$, O—$SO_7$—$R_5$, O—$COOR_5$, OCO—$R_6$, $NR_3$—$CH_2$—$COOR_4$, $NR_3$—$SO_2$—$R_5$, $NR_3$—$COOR_5$ or $NR_3CO$—$R_6$;
$R_3$=H,
n=2
$R_4$=H or a branched or unbranched alkyl group having 1-6 C atoms,
$R_5$=a branched or unbranched alkyl group having 1-7 C atoms which is unsubstituted or substituted by $R_7$, or an aralkyl or heteroaralkyl group which is unsubstituted or substituted by $R_7$,
$R_7$=$NHR_3$, $OR_3$ or —$COOR_4$ and $R_3$ and $R_4$ as defined above
$R_6$=—$COOR_4$, where $R_4$ is as defined above, and
P2=any natural or unnatural α-amino acid of the following structure

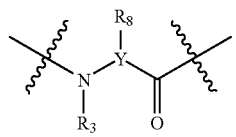

with
$R_3$ as defined above, or a branched or unbranched alkyl group having 1-6 C atoms,
or proline
Y=CH or N,
$R_8$=a branched or unbranched group having 1-8 C atoms, which is unsubstituted or substituted by $R_7$.

15. The method as claimed in claim 11, wherein
$XR_1$=$NR_3$—$CH_2$—$COOR_4$ or $NR_3$—$SO_2$—$R_5$,
$R_3$=H,
n=2
$R_4$=H or ethyl,
$R_5$=branched or unbranched alkyl group having 1-4 C atoms, or an aralkyl or heteroaralkyl group which is unsubstituted or substituted by $R_7$,
$R_7$=$OR_3$ or —$COOR_4$ and $R_3$ and $R_4$ as defined above
P2=any natural or unnatural α-amino acid that is glycine or has the following structure

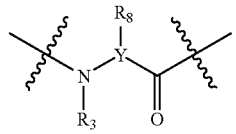

with
$R_3$ as defined above,
Y=CH or N and, in the case of $R_8$=H, may only be N,
$R_8$=H or a branched or unbranched alkyl group having 1-8 C atoms, which is unsubstituted or substituted by $R_7$;
wherein P2 is not glycine alkylated on the nitrogen atom.

16. A pharmaceutical composition comprising a compound of the general formula (I) as claimed in claim 1 and at least one suitable carrier or excipient.

17. The pharmaceutical composition as claimed in claim 16 for oral, subcutaneous, intravenous or transdermal administration for treating thromboembolic disorders.

18. The pharmaceutical composition as claimed in claim 16, wherein the preparation is formulated in the form of tablets, coated tablets, capsules, pellets, suppositories, solutions or patches.

19. A process for producing a pharmaceutical composition comprising mixing a compound of the general formula (I) as claimed in claim 1 and at least one carrier or excipient.

20. The compound of claim 1, wherein
n=2, or
$R_7$=Cl or F, or
$R_6$ is a branched or unbranched alkyl group having 1-4 C atoms; or
$R_8$ is a branched or unbranched alkyl group having 1-4 C atoms.

21. The compound of claim 7, wherein $XR_1$=O—$CH_2$—$COOC_2H_5$ or $NR_3$—$CH_2$—$COOC_2H_5$.

22. The compound of claim 9, wherein $R_8$=a branched or unbranched alkyl group having 1-4 C atoms.

23. The compound of claim 10, wherein $R_8$ is a branched or unbranched alkyl group having 1-4 C atoms.

24. The compound of claim 1, wherein P2 is glycine, serine, glutamic acid, ethyl glutamate, or methyl glutamate.

25. The compound of claim 1, wherein said compound is selected from the group consisting of:

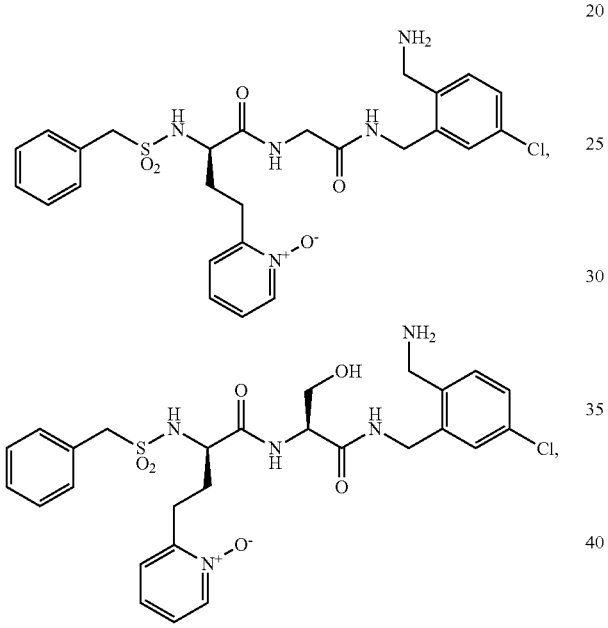

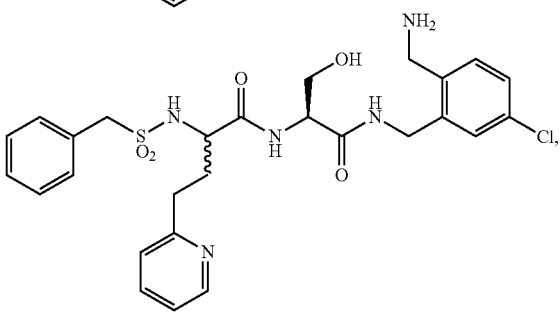

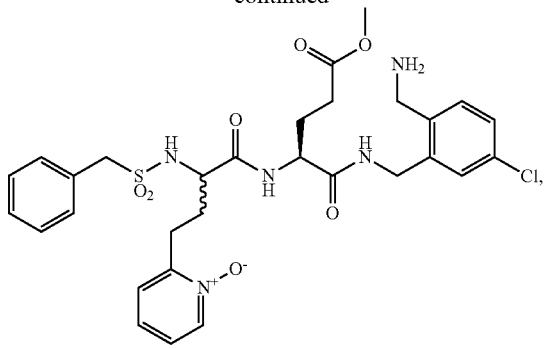

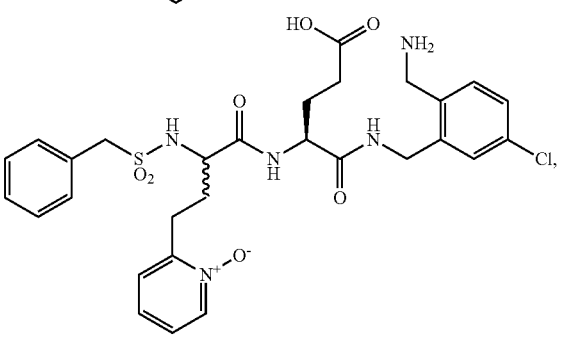

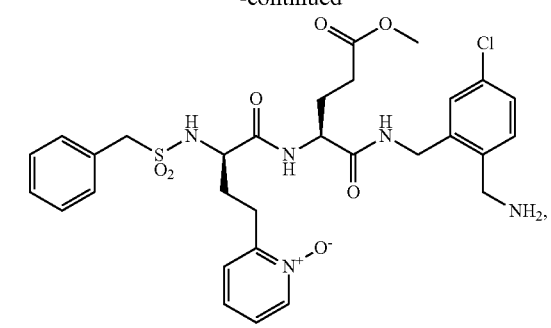
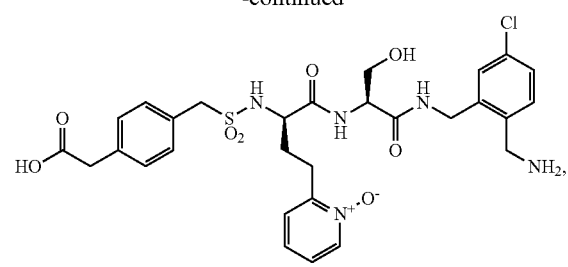
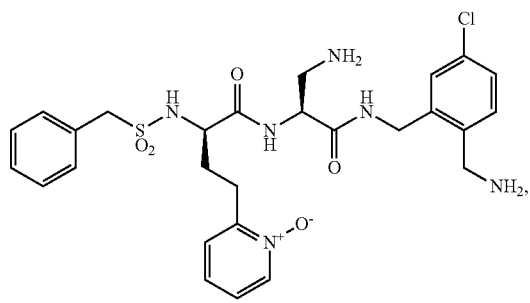
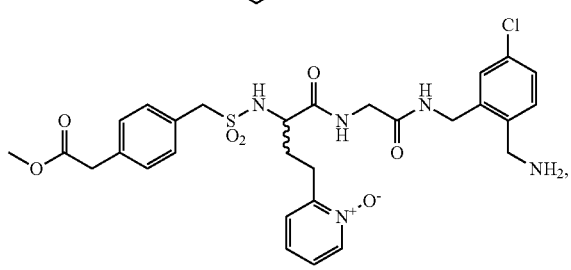
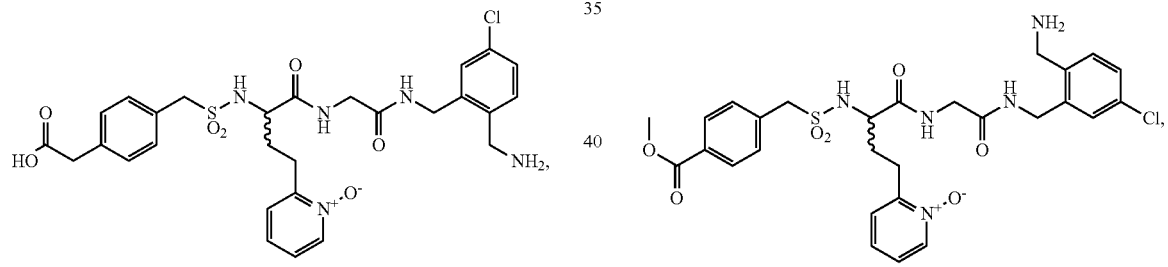
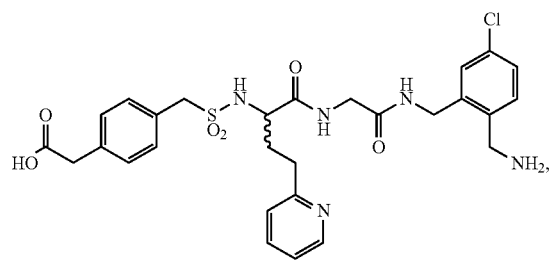
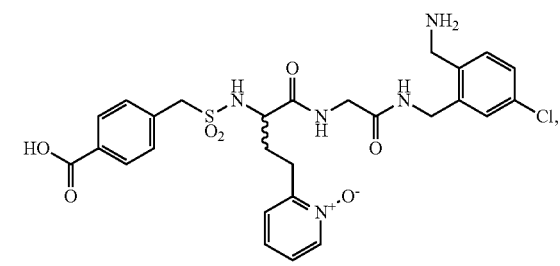
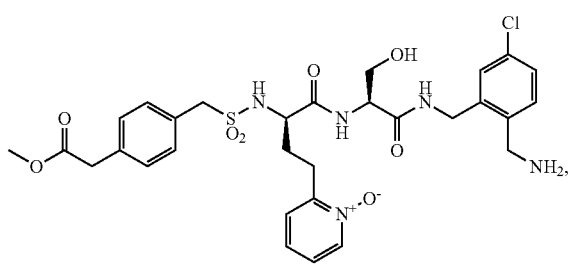
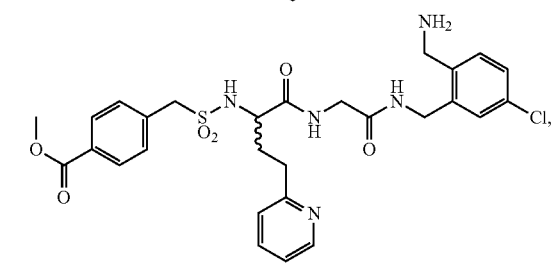

-continued
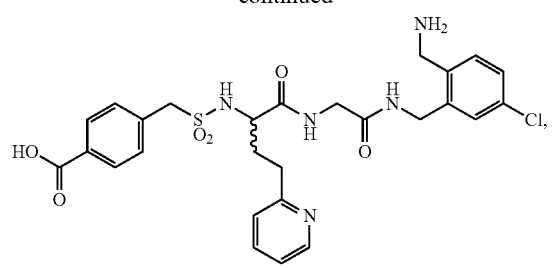
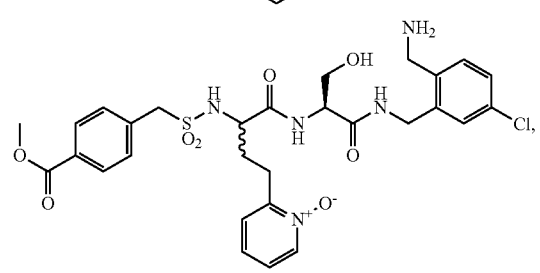
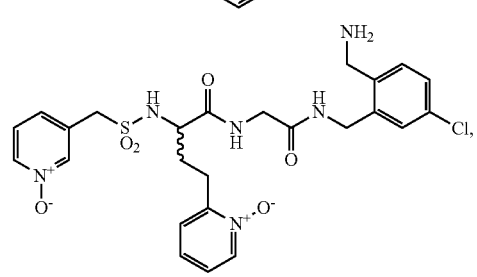
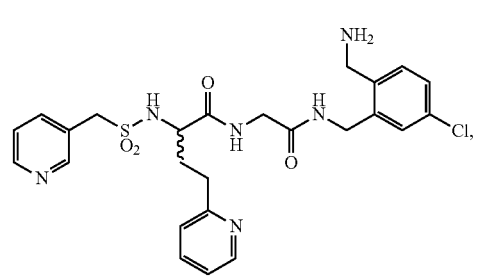
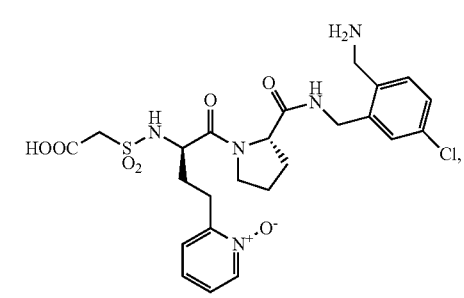
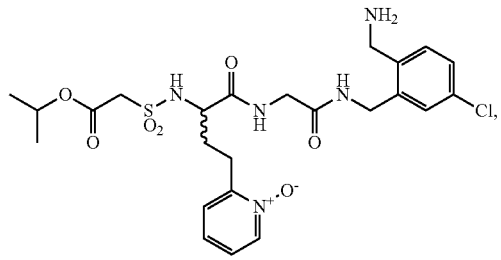
-continued
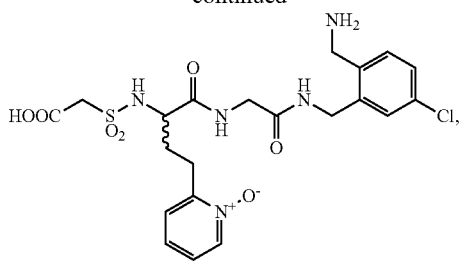
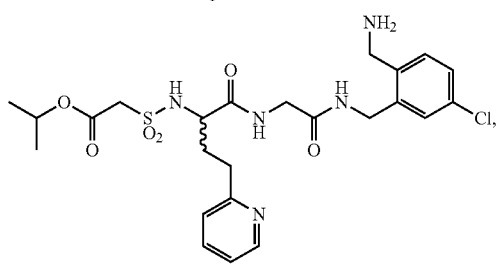
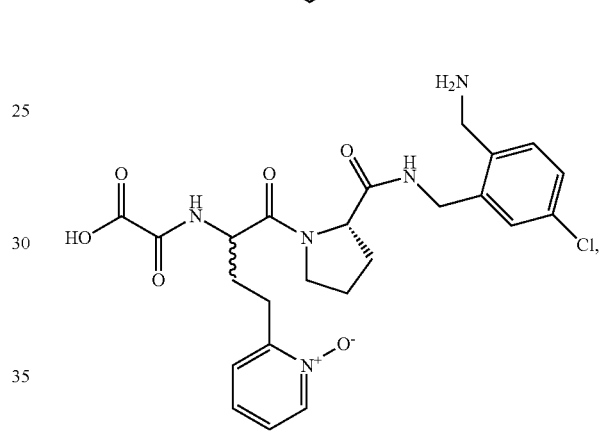
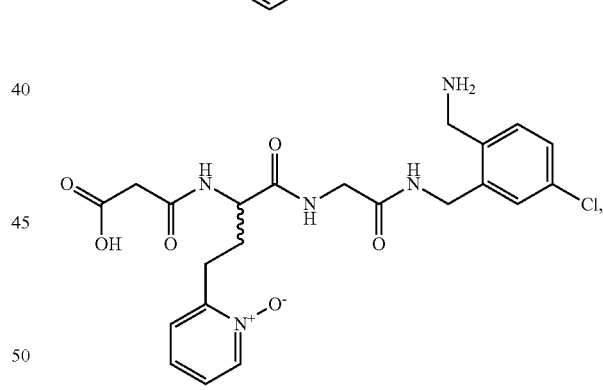
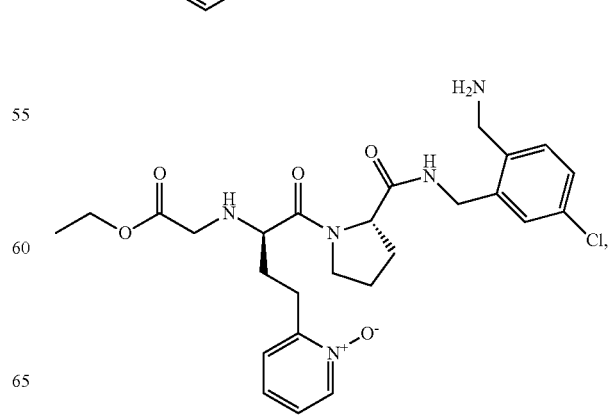

-continued
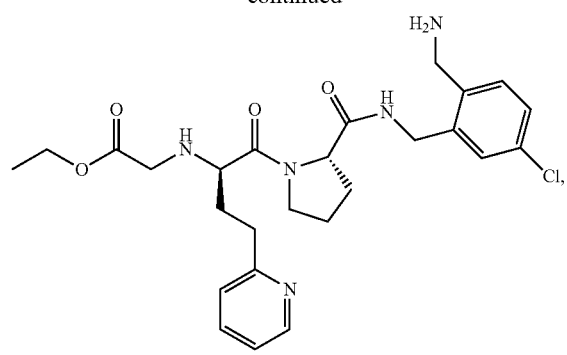
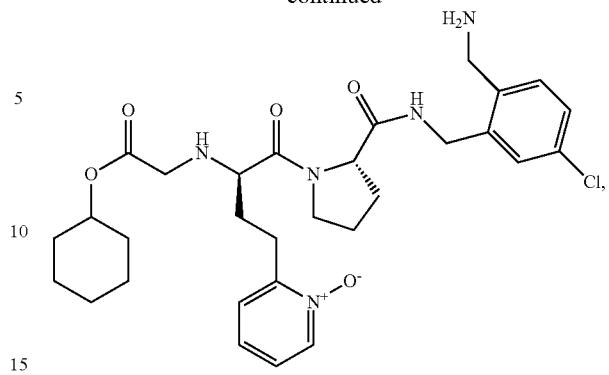
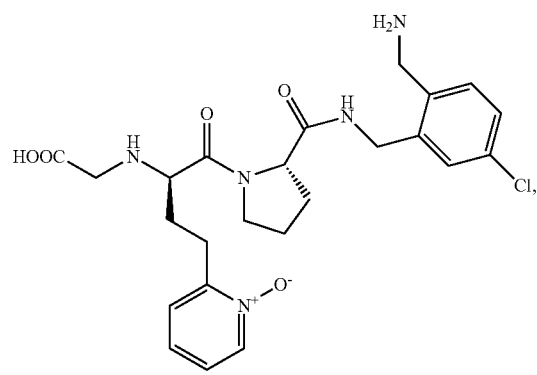
or any pharmaceutically suitable salts thereof.
26. A compound selected from the group consisting of:
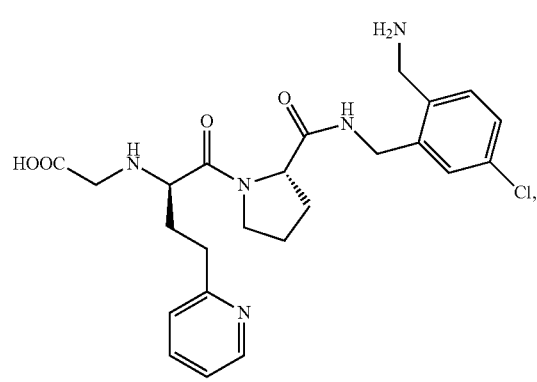
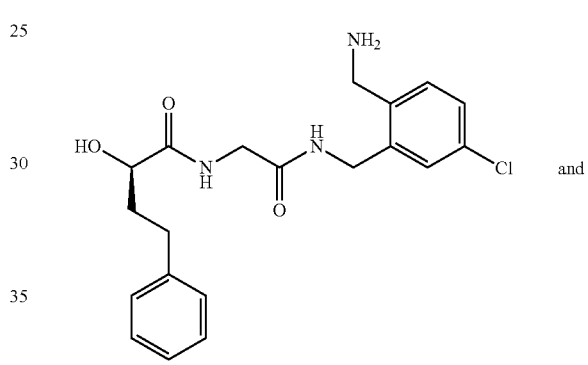 and
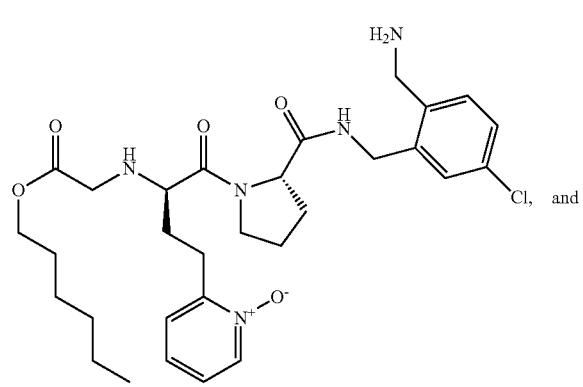, and
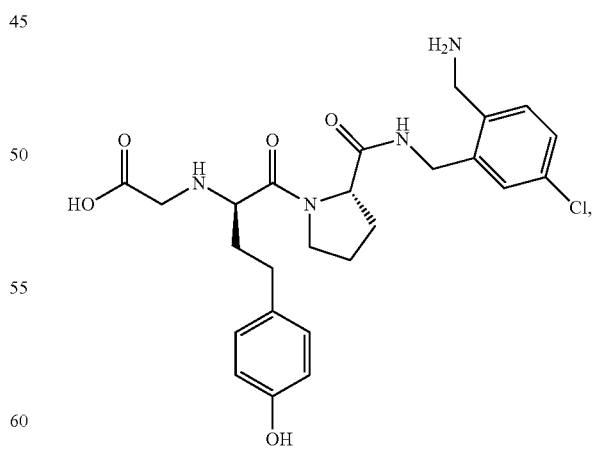
or any pharmaceutically suitable salts thereof.

27. The method of claim 11, wherein
R$_3$ is H or methyl; or
n=2; or
R$_4$=ethyl; or
R$_5$=a branched or unbranched alkyl group having 1-4 C atoms; or
R$_7$=Cl or F; or
R$_6$=a branched or unbranched alkyl group having 1-4 C atoms; or
P2=

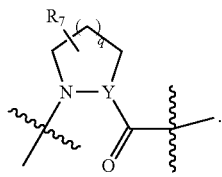

28. The method of claim 12, wherein XR$_1$ is O—CH$_2$—COOC$_2$H$_5$ or NR$_3$—CH$_2$—COOC$_2$H$_5$.

29. The method of claim 14, wherein R$_8$ is a branched or unbranched alkyl group having 1-4 C atoms.

30. The method of claim 15, wherein R$_8$=a branched or unbranched alkyl group having 1-4 C atoms.

31. The compound of claim 1, wherein P2 is glycine or has the following structure,

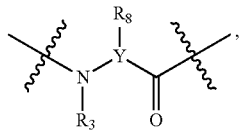

wherein P2 is not glycine alkylated on the nitrogen atom.

* * * * *